US011020527B2

(12) United States Patent
Mikkelsen

(10) Patent No.: US 11,020,527 B2
(45) Date of Patent: Jun. 1, 2021

(54) INJECTOR COMPRISING A SAFETY PIN

(71) Applicant: ALK-Abelló A/S, Hörsholm (DK)

(72) Inventor: Jens Mikkelsen, Ballerup (DK)

(73) Assignee: ALK-ABELLÓ A/S, Hörsholm (DK)

( * ) Notice: Subject to any disclaimer, the term of this patent is extended or adjusted under 35 U.S.C. 154(b) by 339 days.

(21) Appl. No.: 15/736,337

(22) PCT Filed: Jul. 11, 2016

(86) PCT No.: PCT/EP2016/066423
§ 371 (c)(1),
(2) Date: Dec. 14, 2017

(87) PCT Pub. No.: WO2017/009284
PCT Pub. Date: Jan. 19, 2017

(65) Prior Publication Data
US 2018/0185582 A1    Jul. 5, 2018

(30) Foreign Application Priority Data
Jul. 10, 2015   (EP) ..................................... 15176278

(51) Int. Cl.
*A61M 5/20*   (2006.01)
*A61M 5/32*   (2006.01)

(52) U.S. Cl.
CPC .......... *A61M 5/2033* (2013.01); *A61M 5/326* (2013.01); *A61M 2005/206* (2013.01); *A61M 2005/2073* (2013.01)

(58) Field of Classification Search
CPC ................ A61M 5/2033; A61M 5/326; A61M 2005/206; A61M 2005/2073;
(Continued)

(56) References Cited

U.S. PATENT DOCUMENTS

| 4,031,893 A | 6/1977 | Kaplan et al. |
| 5,085,641 A | 2/1992 | Sarnoff et al. |

(Continued)

FOREIGN PATENT DOCUMENTS

| EP | 2 311 510 A1 | 4/2011 |
| WO | WO 86/01120 | 2/1986 |

(Continued)

OTHER PUBLICATIONS

International Search Report and Written Opinion dated Oct. 10, 2015, in PCT International Application No. PCT/EP2016/066423.

*Primary Examiner* — Nathan R Price
*Assistant Examiner* — Dung T Ulsh
(74) *Attorney, Agent, or Firm* — Finnegan, Henderson, Farabow, Garrett & Dunner, L.L.P.

(57) ABSTRACT

An injector is provided for performing an injection operation comprising a housing (104), a needle extendable from a front end of the housing, a rear end of the housing and a longitudinal axis extending between the front end and the rear end, a safety pin (116) in an actuation locked position coupled to the housing and moveable to a safety released position coupled to the housing. The injector is locked against actuation when the safety pin is in the actuation locked position and the injector is ready for actuation of the injection operation when the safety pin is in the safety released position.

18 Claims, 18 Drawing Sheets

(58) Field of Classification Search
CPC ........ A61M 2005/208; A61M 5/31581; A61M 5/31583; A61M 5/31586
See application file for complete search history.

(56) References Cited

U.S. PATENT DOCUMENTS

| | | | |
|---|---|---|---|
| 5,295,965 A | 3/1994 | Wilmot | |
| 2008/0195056 A1* | 8/2008 | Bishop | A61M 5/2033 604/218 |
| 2010/0152659 A1* | 6/2010 | Streit | A61M 5/2033 604/136 |
| 2011/0125100 A1 | 5/2011 | Schwirtz et al. | |
| 2013/0018313 A1* | 1/2013 | Kramer | A61M 5/3007 604/131 |
| 2014/0364812 A1* | 12/2014 | Lumme | A61M 5/3234 604/198 |
| 2017/0080159 A1* | 3/2017 | Wei | A61M 5/31515 |
| 2017/0354779 A1* | 12/2017 | Atterbury | A61M 5/31568 |
| 2018/0207363 A1* | 7/2018 | Fabien | A61M 5/20 |

FOREIGN PATENT DOCUMENTS

| | | |
|---|---|---|
| WO | WO 2007/002052 A2 | 1/2007 |
| WO | WO 2009/097934 A1 | 8/2009 |
| WO | WO 2011/039212 A1 | 4/2011 |
| WO | WO 2012/031627 A1 | 3/2012 |

* cited by examiner

Fig. 30
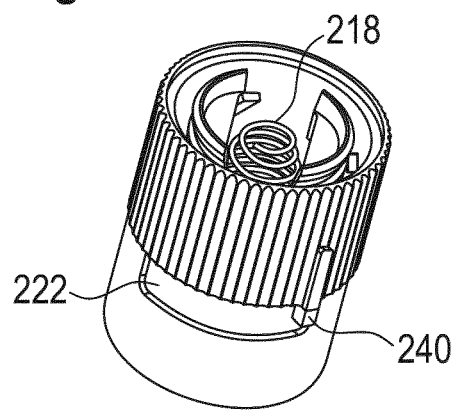
Fig. 31
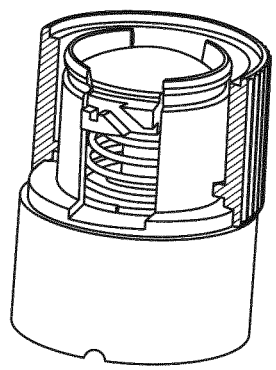
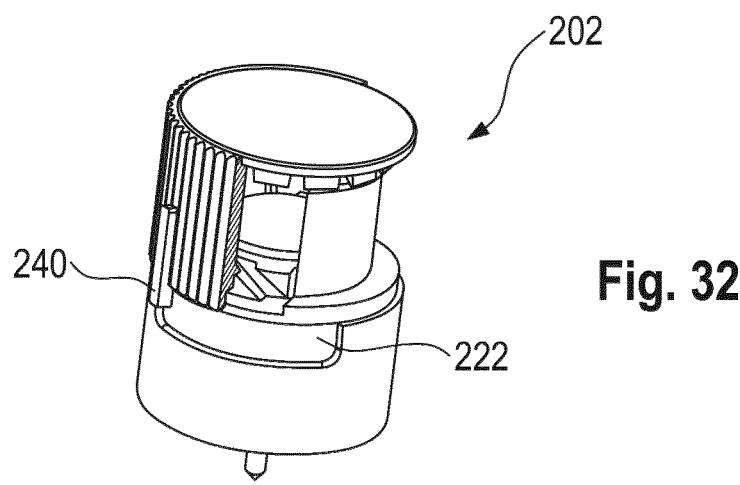
Fig. 32
Fig. 33
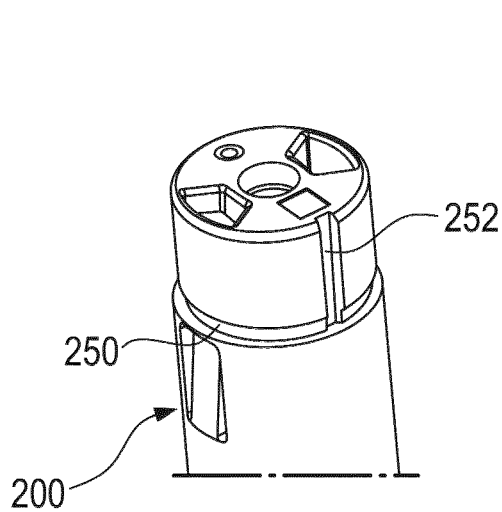
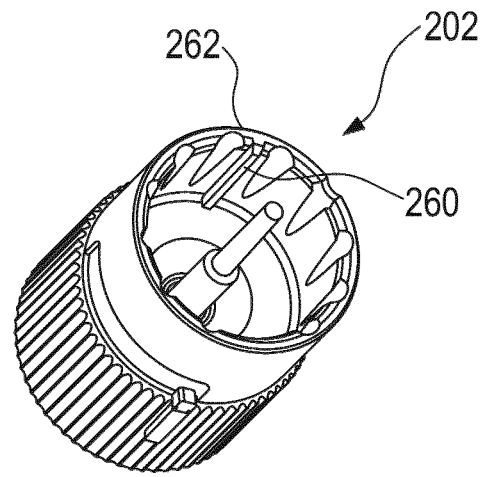
Fig. 34

INJECTOR COMPRISING A SAFETY PIN

CROSS-REFERENCE TO RELATED PATENT APPLICATIONS

This application is a National Stage Entry of International Application No. PCT/EP2016/066423, filed Jul. 11, 2016, which claims priority from European Patent Application No. 15176278.8, filed Jul. 10, 2015. The entire contents of the above-referenced applications are expressly incorporated herein by reference.

FIELD OF THE INVENTION

The present invention relates to an injector, particularly an autoinjector, having a safety pin that is moveable from an actuation locked position in which the injector is locked from actuation, so as to release the lock to ready the injector for actuation.

BACKGROUND OF THE INVENTION

Injectors, particularly autoinjectors, having such a safety pin are known in the art.

US 2011/0125100 A1 discloses an injection device, in particular an autoinjector, comprising a support housing which has a distal end to be applied to a patient and a proximal end opposite the distal end, between which a longitudinal axis extends. The injection device comprises an activating sleeve, which surrounds the support housing at least partly, whereby the distal end of the support housing projects over the activating sleeve, and the activating sleeve can be displaced in an axial direction relative to the support housing. The injection device comprises a cartridge containing the medicine to be administered in an injection procedure, whereby the cartridge is mounted in the support housing, a first drive unit which is in active connection with the cartridge and the activating sleeve and can be triggered by means of the activating sleeve. The injection device of US 2011/0125100 comprises a needle arrangement, which is arranged ahead of the cartridge in the storage position of the injection device.

The first drive unit and holding arms allocated to the driving means are mounted inside the support housing. The holding arms engage in turn in a holding disc arranged in the region of the proximal end of the injection device. The injection device comprises a safety cap comprising a safety cap to prevent the unintentional triggering of the first drive unit, whereby in a centre of the safety cap, there is provided a safety pin penetrating the holding disc. The safety pin locks the holding arms in a radial direction with respect to the longitudinal axis and prevents, until removal of the safety cap together with the safety pin, a release of the holding arms. That is, the safety pin locks the holding arms onto the holding disc in an actuation locked position. It is only once the safety pin has been removed that the lock is released and the injection device is in a ready for actuation state.

After removal of the safety cap with its safety pin, it is possible to displace the ends of the holding arms to release the holding disc. The holding arms are so displaced to release the holding disc upon a relative displacement of the activating sleeve relative to the support housing.

Another injector having a safety pin is known from EP 2311510. In this document, there is disclosed an autoinjector comprising a collet activation structure having a generally cylindrical shape with a sloped collet activation surface located on a free end. The collet activation surface is provided such that when a front end of the autoinjector is forced into an injection site arrowheads of a collet are forced into engagement with the collet activation surface to force the arrowheads of the collet together. One side of each arrowhead is configured to contact and engage a collet retention surface. Sidearms including the arrowheads are able to be deflected inwardly to release the collet retention surface to release a spring assembly and thus release the necessary energy to inject the medicament into a user to permit operation of the auto-injector.

The autoinjector of EP 2311510 also comprises a safety pin based actuation lock. Specifically, an end of the collet adjacent the arrowheads includes an opening sized to receive a safety pin. The safety pin prevents the side arms from being deflected inwardly towards each other. When secured in place, the pin prevents activation of the autoinjector, thereby defining an actuation locked configuration in which the autoinjector is locked against actuation. The safety pin is removed to free the lock and to ready the auto-injector for operation, thereby defining a safety released configuration of the autoinjector in which the autoinjector is ready for actuation.

Other such safety pin arrangements are known in the art from U.S. Pat. Nos. 5,295,965 and 4,031,893.

According to U.S. Pat. No. 5,295,965, in an initial condition of the injector, a drive spring is held in a compressed position by a collet having at their tail ends detent teeth engaging a latch ring. A safety pin normally keeps the teeth apart but when it is withdrawn they can be urged together to release the collet by a short movement of an end cap.

According to U.S. Pat. No. 4,031,893, an injection device comprises elongated fingers terminating in a frusto-conical detent. A notch is formed immediately forward of the detent to provide a square locking face. A gun spring is held in a compressed condition by the square faces of the detents resting on a planar face of an end wall of an inner sleeve. In order to make certain that the frusto-conical detents are not accidentally cammed inwardly, a safety pin assembly is provided. This assembly comprises a cap having a cylindrical sleeve and a safety pin that extends inwardly from the center of the cap into an opening formed by the inner ends of the elongated fingers to thereby prevent inward movement of the detents.

In each of these prior art injectors, and other such injectors having a safety pin that has to be removed to ready the injector for actuation, removal of the safety pin exposes an opening in a proximal or rear end of the injector. That is, after removal of the safety pin, there is exposed a central through opening (aligned with a central longitudinal axis of the injector) in a proximal or rear face of the injector. A user may associate such a central opening with an opening through which a needle is to penetrate during an injection operation. This issue can be exacerbated by modern auto-injectors having a plug or seal in a distal or forward opening of the injector through which the needle passes during injection, thereby providing an injector, after removal of the safety pin, in which the rear end has an opening, but the forward end does not having an opening (or at least not an open one).

There thus exists potential for a user to confuse the correct forward end for placement of the injector against an injection site, particularly because the user may be under stress due to an urgent need for treatment of a physiological condition (such as an allergic reaction to an ingested or otherwise intaken substance to the body) when requiring the injector, e.g. during anaphylactic shock.

EP 2311510 (cited above) offers one solution to this potential problem. In particular, this document discloses a release pin or safety pin removably attached to an actuation assembly to prevent inadvertent actuation of the auto-injector when the release pin is in place. A pin or stem on the release pin is received within an opening in the actuation assembly to prevent actuation of the auto-injector. This opening in a power pack is spaced from the open end of the housing such that the opening is less visible to a user prior to administering the drug. This arrangement is provided so that user will not orient the incorrect end of the auto-injector against the injection surface of the user. The power pack is recessed or spaced from the end of the housing, which provides an indication to the user that pressing the power pack will not operate the auto-injector. The recessed nature of the power pack serves to hide the release pin hole in the power pack when the user is viewing the instructions on the outer body such that the user does not confuse the release pin hole with the opening through which the needle passes for administering the medicament.

In the device of EP 2311510, the opening is hidden when the injector is viewed from the side (i.e. when reading instructions printed on the housing sidewall), but it is still visible when viewed from above (i.e. in most use circumstances). The solution in EP 2311510 does not address the source of the problem, namely that of a pin hole being exposed in a non-injection end of the injector when the safety pin is removed.

Other solutions have been suggested. Commercially available product EPIPEN® has a forwardly disposed arrow pointing in the direction of the forward end of the injector to indicate to a user through which end the needle will penetrate during injection. Further, the forward end is tapered, to provide a nozzle like shape indicating the forward end. The forward end is also coloured brightly as compared to the remainder of the housing. None of these solutions address the source of the problem, namely that of a pin hole being exposed in a non-injection end of the injector when the safety pin is removed.

U.S. Pat. No. 5,085,641 discloses an autoinjector comprising a stressed spring assembly which includes a collet member providing spring fingers with free rearward end portions having generally radially extending locking surfaces engaging a generally radially extending locking surface on a forward tubular housing member. The stressed spring assembly is operable in response to forward movement of a safety actuating pin member to flex inwardly to effect spring biased release of the collet member.

In U.S. Pat. No. 5,085,641, so long as a forward portion of the safety actuating pin member is in a storage position, the spring fingers cannot move transversely inwardly towards one another, thus retaining the locking surfaces in engagement. In use, a user grasps the forward tubular housing member in one hand and extends the thumb of that hand over a thumb-engaging portion of the safety actuating pin member. The safety actuating pin member is forwardly moved until the spring fingers flex by virtue of the pressure between the locking surfaces so that their rearward ends move to a position approaching the surface of an intermediate portion safety actuating pin member adjacent the thumb-engaging portion. When the spring fingers have flexed to this extent, the locking surfaces of the collet member are moved off of the locking surface of the forward tubular housing member, allowing the collet member together with the safety actuating pin member to move forwardly under the action of the spring. When the thumb-engaging portion of the safety actuating pin member reaches the locking surface of the forward tubular housing member, its forward movement is stopped and it is captured in a recess within an end of the forward tubular housing member. In this prior art document, safety release and injector actuation operations are combined in a forward movement of the safety actuation pin member. There is, therefore, a risk that actuation will be inadvertently performed when only safety release was intended. The problem of uncovering a hole in a rear end of the autoinjector as a result of removing a safety pin member prior to actuation is not discussed in this prior art document.

Accordingly, an objective of the present invention is to provide an injector that uses a safety pin having a configuration that locks the injector against actuation and which provides reduced risk of user confusion as to which end is the needle end and which end is the non-injection end. A specific aspect of this problem is to avoid confusion resulting from a pin hole being exposed by removal of the safety pin at the non-injection end of the injector.

SUMMARY OF THE INVENTION

According to the present invention, there is provided an injector for performing an injection operation comprising a housing, a needle extendable from a front end of the housing, a rear end of the housing and a longitudinal axis extending between the front end and the rear end, a safety pin in an actuation locked position coupled to the housing and moveable to a safety released position coupled to the housing, wherein the injector is locked against actuation when the safety pin is in the actuation locked position and the injector is ready for actuation of the injection operation when the safety pin is in the safety released position. The safety pin may be movable along the longitudinal axis (e.g. rearwardly movable) or rotatably movable between the actuation locked and safety released positions.

According to the present invention, the safety pin is in the locked position so that the injector is not able to be actuated. The actuation locked position prevents inadvertent actuation of the injector such as during storage and transport. The safety pin is able to be moved to a released position so that the injector is able to be actuated. In the released position, the injector has not yet been actuated, but is in a configuration whereby the injector is actuation ready. The user, with the safety pin in the safety released position, may then actuate the injector in order to carry out an injection process.

According to the present invention, the safety pin remains coupled to the housing of the injector in the safety released position. In prior art injectors discussed above, the safety pin is removed from the injector, which exposes an opening through which the pin extends, potentially causing confusion as to which end of the injector is the end to be placed against the skin. The present invention avoids this problem by maintaining the safety pin coupled to the housing in the safety released position, i.e. the safety pin is not removed from the injector.

In the safety released position of the safety pin, the injector is ready for actuation of the injection operation, but the injection operation is not yet actuated.

In an embodiment, the pin extends through an opening in a rear end face of the housing, wherein the needle of the injector is extendable through a front end face of the housing. The rear end face extends perpendicularly to the longitudinal axis.

In an embodiment, the opening is covered by a safety cap comprising the safety pin when the safety pin is in the safety released position. In this way, the opening is entirely hidden from view for a user, e.g. a user viewing the injector along the longitudinal axis of the injector from the rear end (i.e. not the front, needle end) of the injector.

In an embodiment, the safety pin remains disposed in the opening in the safety released position.

In an embodiment, the injector comprises an actuator for actuating the injection operation and the safety pin is arranged to lock the actuator in the actuation locked position and is arranged to release the lock to allow operation of the actuator in the safety released position. That is, the actuator is ready for actuation when the safety pin is in the safety released position, but is not yet actuated for actuating the injection operation.

In an embodiment, the actuator comprises an engaged detent mechanism that is disengageable to actuate the injection operation, wherein the detent mechanism is locked to prevent disengagement by the safety pin being in an actuation locked position, and wherein the safety pin is movable to the safety released position in which the detent mechanism is still engaged, yet the detent mechanism is unlocked and is thus able to be disengaged to actuate the injection operation.

In an embodiment, the actuator comprises at least one resilient arm that is deflectable to release from a holding surface to actuate the injection operation with the injector, wherein the safety pin is arranged to block deflection of the at least one resilient arm in the actuation locked position and to free deflection of the at least one resilient arm in the safety released position. The at least one resilient arm remains engaged with the holding surface when the safety pin is moved to the safety released position. The holding surface and the resilient arm may be comprised in the above detent mechanism.

In an embodiment, the at least one resilient arm comprises plural resilient arms that are deflectable toward one another to release from a holding surface to actuate the injection operation of the injector, wherein the safety pin is arranged to block deflection of the resilient arms toward one another in the actuation locked position and to allow such deflection in the safety released position. The resilient arms remain engaged with the holding surface when the safety pin is in the safety released position prior to actuation of the injector.

In an embodiment, the resilient arms are comprised in a collet of the injector.

In an embodiment, the resilient arms define a passage therebetween, wherein the safety pin extends into the passage in the actuation locked position.

In an embodiment, the above described detent mechanism may comprise a collet and collet retention surface from which the collet is disengagable to actuate the injection operation. The safety pin is disposed so as to lock the collet in an engaged position with the collet retention surface when the safety pin is in the actuation locked position and to allow disengagement when the safety pin is in the safety released position. An end of the collet is deflectable to disengage from the collet retention surface.

In an embodiment, the collet comprises detent teeth (e.g. at a rear end of the collet) that engage the retention surface, thereby forming a latch, and the teeth are disengagable from the retention surface to actuate the injection operation. The safety pin is operable to keep the detent teeth apart when in the actuation locked position to lock the detent teeth in engagement with the retention surface, i.e. to lock the teeth against disengagement therefrom.

In an embodiment, the actuator comprises an outer housing of the injector that is axially moveable relative to a front end of the injector to actuate the injection operation. The axial movement of the outer housing may be a forward movement relative to the front end of the injector.

In an embodiment, the relative movement of the outer housing is operable to disengage the detent mechanism.

In an embodiment, the relative movement of the outer housing is operable to deflect the at least one resilient arm to disengage the holding arm from the holding surface.

In an embodiment, the injection operation of the injector is actuatable by pressing the front end of the injector against an injection site when the safety pin is in the safety released position.

In an embodiment, the injector is an autoinjector.

The autoinjector is configured to automatically perform the injection operation upon actuation. The mechanisms for implementing such an autoinjector are well known in the art. The safety pin of the present invention is applicable to known autoinjectors making use of such a safety feature for locking the autoinjector against actuation and which is configurable to undo the lock to ready the autoinjector for actuation. Thus, the present invention is applicable at least to the autoinjectors known from US 2011/0125100, EP 2311510, U.S. Pat. Nos. 5,295,965 and 4,031,893 described above. Such autoinjectors are hereby incorporated by reference, and should be modified for conformity with the present invention according to the teachings herein, namely to provide a non-removable safety pin that moves from an actuation locked position to a safety released position as prescribed herein.

In an embodiment, the autoinjector comprises a cartridge containing a medicament, a needle, a plunger and a driver for providing a drive force to move the needle from a retracted position relative to the front end to an extended position in which the needle extends beyond the front end and to drive the plunger to eject medicament from the cartridge through the needle when the needle is in the extended position.

In an embodiment, the cartridge has a closed front end prior to actuation of the injector and an open rear for receiving the plunger.

In an embodiment, the cartridge and the needle are moveable in conjunction by the driving force.

In an embodiment, the cartridge is moveable by the driving force from a position spaced from a rear end of the needle to a position in which the medicament in the cartridge is in fluid communication with the rear end of the needle, and thereafter the needle and the cartridge are moveable by the driving force in conjunction to move the needle from the retracted position to the extended position.

In an embodiment, the autoinjector comprises a needle cover that is moveable between a retracted position to a needle covering position when the needle is in the extended position.

In an embodiment, the autoinjector is configured to automatically move the needle cover from the retracted position to the needle covering position upon actuation of the autoinjector.

In an embodiment, the autoinjector comprises a first locking mechanism for locking the needle cover in the retracted position and a second locking mechanism for locking the needle cover in the extended position, wherein the injector is configured, upon actuation of the autoinjector, to unlock the first locking mechanism to allow the needle cover to move to the extended position from the retracted position and to operate the second locking mechanism to lock the needle cover in the extended position for preventing exposure of the needle after the injection operation and after the autoinjector has been moved away from the injection site. Such locking mechanisms are known in the art, such as from EP 23111510 and US 20110125100.

In an embodiment, the autoinjector comprises a needle cover spring for driving movement of the needle cover from the retracted position to the extended position. When present, the needle cover spring is able to drive movement of the needle cover when the first locking mechanism is unlocked.

In an embodiment, the front end comprises a plugged or sealed opening through which the needle extends during the injection operation. The needle is configured to pierce the plug or seal during the injection operation.

In an embodiment, the injector comprises a driver held in a relatively high potential energy state and is configured so that the potential energy is realised after actuation of the injection operation, e.g. after actuation of the actuator, to drive the injection operation automatically.

In an embodiment, the injector comprises a medicament source and a needle, and the injection operation comprises penetration of the needle at the injection site and injection of medicament from the medicament source.

In embodiments, the medicament source contains adrenalin for injection.

In embodiments, the injector is for treatment of anaphylaxis and contains medicament prescribed therefor.

In an embodiment, the driver comprises a spring configured to be held in a compressed state until actuation, e.g. held in a compressed state until released by operation of the actuator.

In an embodiment, the injector comprises an outer housing for grasping by a user.

In embodiments comprising the outer housing and the needle cover, the needle cover is disposed at least partly within the outer housing in the retracted and in the extended positions. In embodiments also comprising the cartridge, there is provided a cartridge housing and the needle cover is disposed at least partly between the outer housing and the cartridge housing in both the retracted and the extended positions. In embodiments comprising the first and second locking mechanisms, the first and/or the second locking mechanisms are disposed between the cartridge housing and the outer housing.

In an embodiment, the pin is elongate and extends along the longitudinal axis of the injector.

In an embodiment, the pin extends along a central longitudinal axis of the injector.

In an embodiment, the safety pin is moveable along the longitudinal axis between the actuation locked position and the safety released position.

In an embodiment, the injector comprises a safety cap comprising the safety pin and a sleeve extending over a rear end portion of the housing of the injector. The safety cap is non-removable by a user. Put another way, the safety cap is engaged with the housing to prevent rearward movement thereof when the safety pin is in the safety released position. This may be achieved by interfacing holding surfaces between the housing and the safety cap for preventing movement of the safety cap in the rearward direction when the safety pin is in the safety released position.

In an embodiment, the safety cap is mounted to the housing via the sleeve.

In an embodiment, the injector comprises a structural guide and structure cooperating with the guide to guide movement of the safety pin between the actuation locked position and the safety released position.

In an embodiment, the guide extends from a first position corresponding to the actuation locked position and a second position corresponding to the safety released position.

In an embodiment, the guide and structure cooperating with the guide comprises a groove and a cooperating projection for riding therein or a projecting thread and a cooperating groove.

In an embodiment, the groove or the thread extend helically or diagonally relative to the longitudinal axis.

In an embodiment, the groove and the cooperating projection are disposed between the outer surface of the housing and the inner surface of the sleeve of the safety cap.

In an embodiment, the groove is defined in an outer surface of the housing and the projection is defined on an inner surface of the sleeve of the safety cap.

In an embodiment, the safety cap comprises a rotatable part for rotation by a user and an axially moveable part connected to the safety pin for moving the safety pin between the actuation locked and safety released positions, wherein the thread and the cooperating groove are disposed between the rotatable part and the axially moveable part.

In an embodiment, the groove is defined in an outer surface of the axially movable part and the thread is defined on an inner surface of the rotatable part.

In an embodiment, the injector comprises a safety pin mover that is manually operable to move the safety pin between the actuation locked position and the safety released position. That is, the safety pin mover is disposed on the injector so as to be graspable to affect movement of the safety pin.

In an embodiment, the safety pin mover comprises a movable part, preferably a rotatable part, operable by a user to move the safety pin between the actuation locked and safety released positions.

In an embodiment, the safety cap comprises a rear cover portion and the safety pin is disposed on a front side of the rear cover portion, preferably disposed centrally with respect to the rear cover portion.

In an embodiment, the safety cap comprising the safety pin covers a rear end face of the housing.

The safety cap is constructed so as to present a closed or solid rear surface at the rear end, e.g. one that does not have a through opening or other open area on a central longitudinal axis of the injector. Put alternatively, the safety cap has a closed or solid rear surface in an area longitudinally aligned with the safety pin when the safety pin is in the safety released position.

In an embodiment, the safety pin mover comprises a rotatable part to affect axial movement of the safety pin between the actuation locked and safety released positions.

In an embodiment, the rotatable part of the safety pin mover is manually graspable, e.g. is externally positioned on the injector to allow manual grasping, to affect at least part of the rotational movement thereof.

In an embodiment, the injector comprises a helical or diagonal, relative to the longitudinal axis, thread for transmitting rotational movement of the rotatable part of the safety pin mover to axial movement of the safety pin. The thread may be implemented by way of a rib, a groove, a slot, or the like.

In an embodiment, the injector defines first and second stop positions corresponding respectively to the actuation locked position of the safety pin and the safety released position of the safety pin. Movement of the rotatable part of the safety pin mover is limited by the stop positions.

In an embodiment, the safety cap comprises a groove, a thread, a slot or other guide structure and complementary structure for running along the groove, thread, slot or other guide structure between the first and second stop positions.

In an embodiment, the guide and complementary structure comprise a groove and a complementary projection in the housing, which is comprised in the safety pin mover, and the safety pin mover or a groove and a complementary thread in an axially translatable part of the safety pin mover and a rotatable part of the safety pin mover.

In an embodiment, the injector comprises a detent arrangement for holding the safety pin mover in at least one of the first and second stop positions. The detent arrangement provides a force bump for holding the safety pin mover in the stop position. For example, the detent arrangement may comprise a resilient protrusion and recess arrangement, cooperating resilient protrusions, or other resilient snap cooperation arrangement. The detent arrangement parts for the first position prevent accidental unlocking of actuation of the injector. The detent arrangement parts for the second position provide a tactile indication to the user that the safety pin is in the safety released position, as well as maintaining the safety pin mover in the second stop position corresponding to the safety released position of the safety pin.

In an embodiment, a first part of the detent arrangement is disposed on a rotatable part of the safety pin mover and a complementary interacting part is associated with a non-rotating part of the safety pin mover, such as the housing of the injector or an axially translatable part of the safety pin mover.

In an embodiment, the safety pin mover comprises the guide and the complementary structure, which are arranged in the sleeve of the safety cap and the housing of the injector and the safety cap itself is rotatable to provide the rotatable part of the safety pin mover.

In an alternative embodiment, the safety pin mover comprises an axially movable, preferably translatable, part and the safety pin mover comprises a rotatable part that cooperate so that rotation of the rotatable part causes axial translation of the axially translatable part, to thereby axially translate the safety pin from the actuation locked position to the safety released position. In this way, the safety pin can be moved out of the actuation locked position without itself being rotated. In this context, axial translation should be understood relative to the longitudinal axis of the injector, e.g. a central longitudinal axis thereof. Translation is to be understood as axial movement of the safety pin without rotation thereof.

In an embodiment, the safety cap comprises the safety pin mover.

In an embodiment, the rotatable part is mounted for rotation without axial movement, i.e. pure rotation.

In an embodiment, the safety pin is fixed to the axially translatable part.

In an embodiment, the safety cap comprises at least one axially extending guide that cooperates with the axially translatable part to guide axial movement of the axially translatable part.

In an embodiment, the axially translatable part and the rotatable part may threadably cooperate to transform rotation of the rotatable part to axial translation of the axially translatable part.

In an embodiment, the safety cap itself or the housing and the safety cap comprise a nut and thread arrangement or other cooperating structure operable to transform rotational input from a user to axial movement of the safety pin between the actuation locked and safety released positions.

In an embodiment, the injector comprises an indicator for indicating when the safety pin is in the safety released position.

In an embodiment, the injector comprises an indicator for visually indicating when the safety pin is in the actuation locked position In an embodiment, the injector comprises an indicator for indicating when the safety pin is in the actuation locked position and when the safety pin is in the safety released position in a visually differentiable way.

In an embodiment, the indicator comprises a moving portion fixedly associated with the movable or rotatable part of the safety pin mover for aligning with or exposing a first stationary portion of the indicator when the safety pin mover is in a position corresponding to the safety released position of the safety pin.

In an embodiment, the indicator comprises a second stationary portion visually differentiable from the first stationary portion, wherein the moving portion is aligned with or exposes the second stationary portion when the safety pin mover is in a first position corresponding to the actuation locked position. The first and second stationary portions may comprise different indicia of any kind, such as different colors, different characters, etc.

In an embodiment, the moving portion comprises a cover that covers the first stationary portion when the safety pin mover is in the actuation locked position In an embodiment, the moving portion may comprise a window, a flag, a tab, a relatively colored area, an identifiable shape, a character, etc.

In an embodiment, the safety pin mover comprises a ribbed gripping surface.

In an embodiment, the safety cap comprises a spring for biasing the safety pin from the actuation locked position to the safety released position.

The injector may comprise a detent arrangement for holding the safety pin in the actuation locked position against the bias of the spring. The detent arrangement may be releasable by manual input from a user. For example, the detent arrangement may comprise a resilient protrusion and recess arrangement, cooperating resilient protrusions, or other resilient snap cooperation arrangement In an embodiment, the spring is operable so as to move, e.g. automatically (that is, without further manual operation), the safety pin to the safety released position once the detent arrangement has been released. Thus, the spring is operable to complete movement from the actuation locked position to the safety released position without further user applied force after the detent arrangement has been released.

In an embodiment, the spring is held in a contracted position by the detent arrangement and be expandable to move the safety pin from the actuation locked position to the safety released position.

In an embodiment, the safety cap is operable to axially move the safety pin between the actuation locked and safety released positions, wherein the safety cap covers the safety pin in the actuation locked and safety released positions. Put another way, the safety cap remains axially stationary and is operable to axially move the safety pin between the actuation locked and safety released positions within the safety cap. In an embodiment, the safety cap hides axial movement of the safety pin. In this way, an axial profile of the injector remains unchanged by axially moving the safety pin.

In embodiments whereby the safety pin moves axially, the safety pin is moveable from the actuation locked position to the safety released position by translation, i.e. without rotation.

In various embodiments, the safety pin is rotatable between the actuation locked position coupled to the housing and the safety released position coupled to the housing. The safety pin may not move axially in rotating between the locked and released positions. Thus, the safety pin is associated with a rotatable part as described above to allow an operative to grasp the rotatable part and cause rotation of the safety pin. The safety pin may form part of a safety cap as described above, which may itself be rotatable to affect rotation of the safety pin. The safety pin may include one or more blocking surfaces that lock against an actuator (e.g. as described above) of the injection device and that move from locking against the actuator when rotated, thereby providing the actuation locked and safety released positions. The safety pin may include, disposed around a circumference of the safety pin, one or more blocking surfaces and one or more recesses (recessed relative to the blocking surfaces), wherein the one or more blocking surfaces engage an actuator of the injection device and the one or more recesses release the actuator, thereby providing the actuation locked and safety released positions when the safety pin is rotated.

For example, the actuator may comprise at least one resilient arm that is deflectable to release from a holding surface to actuate the injection operation with the injector, wherein the one or more blocking surfaces of the safety pin are arranged to block deflection of the at least one resilient arm in the actuation locked position and the one or more recesses is configured to free deflection of the at least one resilient arm in the safety released position. The safety pin is rotatable to bring either the one or more holding surfaces into alignment with the at least one resilient arm or to bring the one or more recesses into alignment with the at least one resilient arm.

In another aspect of the present invention, a safety cap is provided. The safety cap comprises a sleeve for receiving therein a rear end portion of a housing of an injector for mounting the safety cap to the injector, and a safety pin for extending through an opening in the rear end of the housing of the injector to lock an actuator of the injector, and a safety pin mover, wherein the safety pin mover comprises at least one of a thread and structure for cooperating with the thread to transform rotational movement of a rotatable part of the safety pin mover to rearward axial movement of the safety pin for rearwardly moving the safety pin from an actuation locked position in locking relation with the actuator and a safety released position in which the actuator is unlocked by the safety pin.

In an embodiment, the rotatable part of the safety pin mover is rotatable to affect axial translation of the safety pin.

In an embodiment, the rotatable part of the safety pin mover is rotatably mounted relative to the sleeve.

In an embodiment, the safety pin is mounted for axial movement relative to the sleeve.

In an embodiment, the sleeve is adapted for resilient snap fit mounting to the housing of the injector. For example, the sleeve may comprise one part of a resilient snap fit mechanism comprising a protrusion part and a recess or opening part for receiving the protrusion part therein.

In an embodiment, the safety cap comprises an axially translatable part to which the safety pin is fixed and which cooperate through the thread and thread cooperating structure with the rotatable part of the safety pin mover such that rotation of the rotatable part of the safety pin mover causes translation of the safety pin.

In an embodiment, the safety cap comprises a visual indication part in fixed relation with the rotatable part of the safety pin mover, wherein the visual indication part comprises a relatively coloured area, a flag, a tab, a window, an icon or other visual indicia for indicating when the safety pin is in the safety released position.

In an embodiment, the safety cap comprises complementary visual indicator part including a moving part that is in fixed relation with the rotatable part of the safety pin mover and first and second stationary parts that are visually distinct, wherein the moving part aligns with the first stationary part when the safety pin is in the actuation locked position and wherein the moving part aligns with the second stationary part when the safety pin is in the safety released position.

In an embodiment, the safety pin and the sleeve are coaxially arranged.

In an embodiment, the safety cap comprises a closed rear cover portion at least in an area axially aligned with a longitudinal axis of the safety pin.

In an embodiment, the rotatable part of the safety pin mover comprises ribs for enhancing a user's grip thereof.

In an embodiment, the rotatable part of the safety pin mover is externally accessible for being gripped and rotated by a user.

In an embodiment, the rotatable part of the safety pin mover is rotatable between first and second stop positions corresponding respectively to the safety pin being in the actuation locked position and the safety pin being in the safety released position.

In an embodiment, the safety cap comprises at least one of first and second detent arrangements for holding the first and second stop positions and requiring a force bump to release the detent arrangements.

In an embodiment, the safety cap comprises a spring for biasing the safety pin to the safety released position relative to the sleeve.

In an embodiment, the pin and the sleeve define a loop shaped, e.g. annular, space therebetween into which the rear end portion of the housing of the injector is able to be inserted to mount the safety cap to the injector.

In an embodiment, the thread comprises a rib arranged as a thread or a groove arranged as a thread.

In an embodiment, the thread extends helically or diagonally.

In an embodiment, the cooperating structure comprises a groove for receiving the rib formed as a thread to allow the rib to ride in the groove or a projection for riding in the groove formed as a thread.

The features of the safety cap disclosed above with respect to the injector aspect of the invention are applicable to the safety cap aspect of the invention and vice versa.

BRIEF DESCRIPTION OF THE FIGURES

FIG. 14 shows a start or first position along the thread at which the safety cap is held by engaged stop surfaces, corresponding to the actuation locked position. FIG. 15 shows an end or second position along the thread at which the safety cap is held by engaged stop surfaces, corresponding to the safety released position.

FIGS. 30 to 32 show the safety cap at different stages of assembly.

FIGS. 33 and 34 show features allowing the safety cap to be mounted to an injector.

DETAILED DESCRIPTION OF PREFERRED EMBODIMENTS

Figure 1:
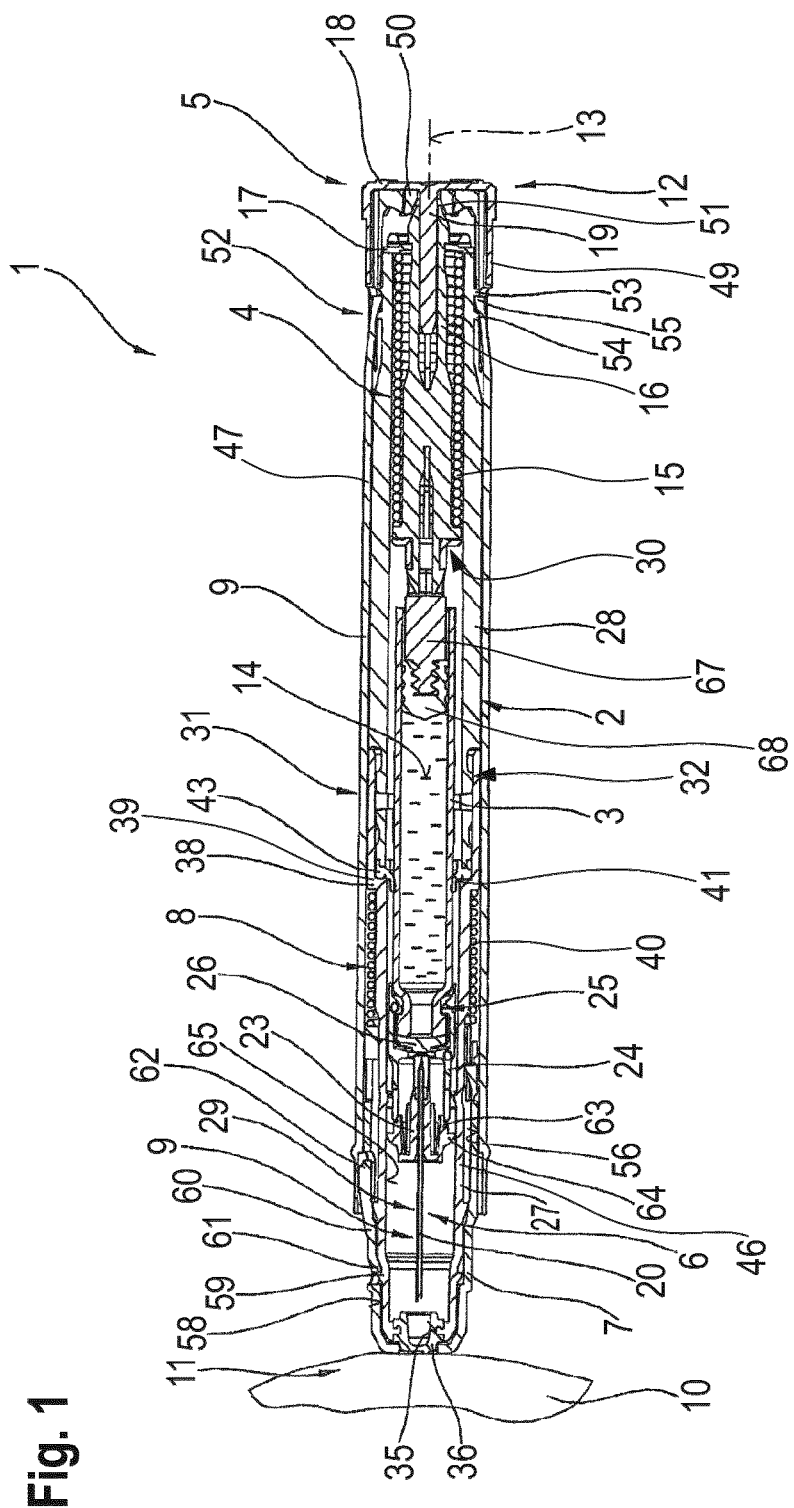
FIG. 1 shows an injection device that is in accordance with an embodiment of the present invention except that the safety cap is removable, in axial cross section and simplified representation.
Figure 2:
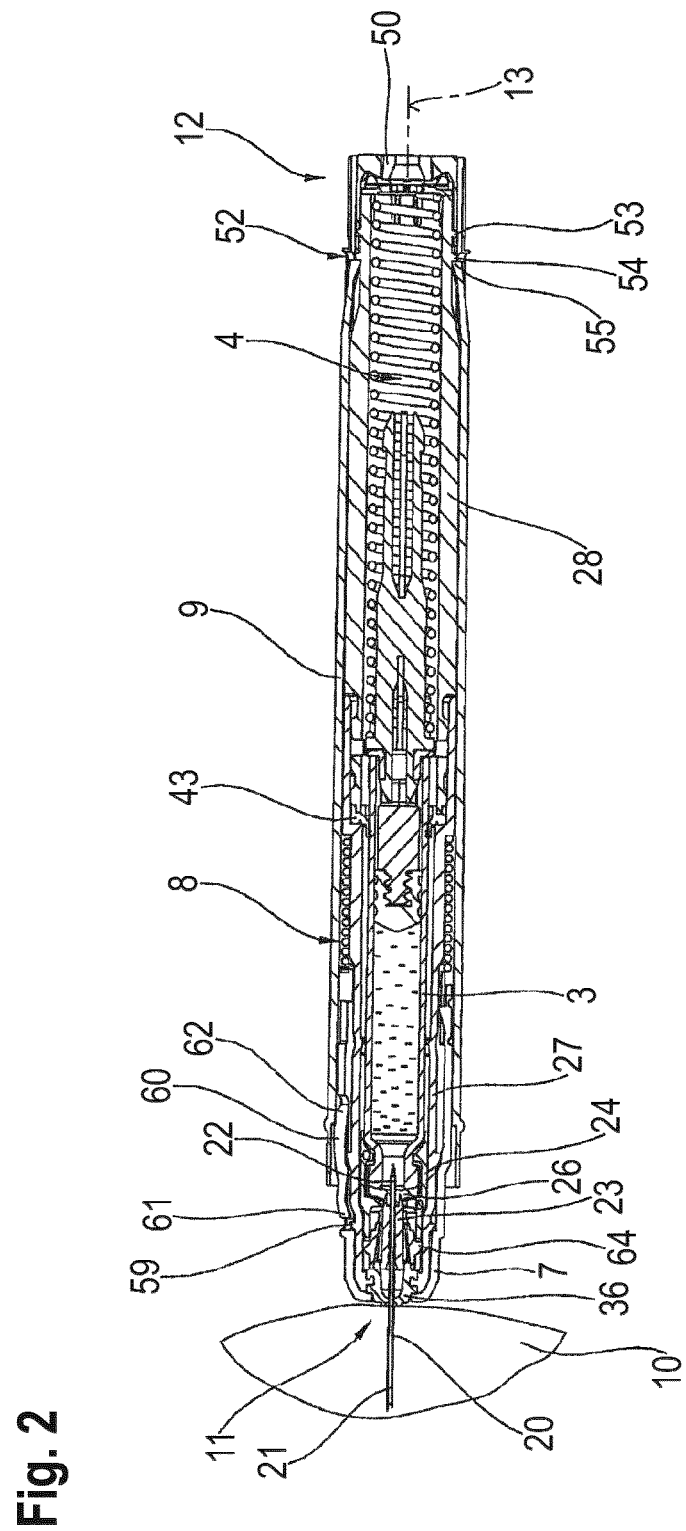
FIG. 2 shows the injection device according to FIG. 1, during the administration procedure of the medicine, in axial cross section and simplified representation.

In FIGS. 1 to 10, an injection device (or injector) known from US 2011/0125100 is shown. This prior art injection device is described in detail in the following to provide a full account in the present application of the structure and workings of such an injection device. The safety cap 18 and safety pin 19 shown in these figures, and described in the following, are not, however, according to an embodiment of the present invention since they are removable. This prior art arrangement of the cap 18 and safety pin 19 is included for the purpose of discussing drawbacks in the removable kind of safety cap/safety pin to illustrate the contribution made by the non-removable safety pin shown from FIG. 11 onwards and described in detail herein with respect thereto. This same modification of the autoinjector of US 2011/0125100 to replace the known removable safety pin with a safety feature according to FIG. 11 onwards (and described below) can be applied to other known autoinjectors where applicable to provide an improved safety autoinjector having a non-removable safety pin that nonetheless is transitionable from an actuation locked configuration for the autoinjector to a safety released configuration.

In FIGS. 1 to 4 an injection device 1 (injector), in particular an autoinjector, is shown in simplified form in different operating positions. Such autoinjectors are used for the automatic administration of a medicine The injection device 1 is composed of a plurality of components and can comprise a support housing 2, a storage container mounted therein such as a cartridge 3, a first releasable drive unit 4 (a driver), which is in active connection with the cartridge 3, a safety device 5, a needle arrangement 6, a needle protection element 7 (needle cover) and a second drive unit 8 assigned to the needle protection element 7 and thus in active connection therewith and an activating sleeve 9 (the outer housing). The support housing 2 and the activating sleeve 9 can be considered as comprised in a general housing of the injection device or injector 1.

The injection device 1 i.e. the support housing 2 comprises a distal (front) end 11 to be applied to the living being such as a patient 10 and a proximal (rear) end 12 averted therefrom, whereby a longitudinal axis 13 extends between the two ends 11, 12. Furthermore, in the description of the position front and rear is used and thereby the front is allocated to the distal end 11 and rear to the proximal end 12. The holding container for a medicine 14 is formed here by the cartridge 3, in which the medicine 14 or the active ingredient to be administered or injected is already stored during the storage position and is ready to be administered. The cartridge 3 is thereby mounted in the support housing 2 and surrounded by the latter. The cartridge 3 is a conventional packaging for medicine 14, whereby the amount of medicine 14 held therein can be adjusted to the respective application. Furthermore, in a known manner the first triggerable (actuatable) drive unit 4 (driver) is assigned to the cartridge 3 at the end facing the proximal end 12 of the injection device 1 or is in active connection therewith.

The first drive unit 4 comprises a first driving means 15 (spring), which is secured by the safety device 5 against release until the user actively actuates the injection device 1, in which the first drive unit 4 is released and thus the injection device 1 is triggered (actuated). By means of the safety device 5 thus the first drive unit 4 is secured in its position relative to the support housing 2 prior its activation for the injection procedure. The first drive unit 4, in particular the driving means 15 and the holding arms 16 allocated to the driving means 15 are mounted inside the support housing 2. The holding arms 16 engage in turn in a holding disc 17 (comprising a holding surface) arranged in the region of the proximal end 12 of the injection device 1, whereby a detailed description thereof is given in the following. The first drive unit 4, the support housing 2, the holding arms 16 and the holding disc 17 can be considered comprised in a general actuator. The injection device 1 comprises a safety cap 18 to prevent the unintentional triggering of the drive unit 4, whereby in its centre a safety pin 19 penetrating the holding disc 17 is arranged. The safety pin 19 locks the holding arms 16 in the radial direction in a known manner with respect to the longitudinal axis 13 and prevents release of the holding arms from the holding surface of the holding disc 17, thereby placing the injection device 1 in an actuation locked state. Only after removal of the safety cap 18 together with the safety pin 19 are the holding arms 16 unlocked from the holding disc 17 to place the injection device 1 in an actuation ready state or safety released state. Even in the actuation ready state, the holding arms 16 are held on the holding surface of the holding disc 17, but are free to be deflected in radial direction of the longitudinal axis 13 for actuation of the injection device 1.

In the region of the distal end 11 the needle arrangement 6 is arranged directly before the cartridge 3. The needle arrangement 6 comprises in turn a cannula 20 or a hollow needle with needle ends 21, 22 spaced apart from one another in the direction of the longitudinal axis 13. The cannula is held in turn by a needle support 23 and is mounted in the latter. Both needle ends 21, 22 project respectively on both sides of the needle support 23.

The needle support 23 is coupled in turn via a guiding element 24 to a cartridge end 25 facing the distal end 11 or is connected therewith. For further details see also the following FIGS. 6 and 7. The cartridge 3 in turn has at the cartridge end 25 facing the distal end 11 a penetrable cartridge seal 26. The proximal needle end 22 facing the cartridge seal 26 is arranged by means of the needle support 23 on the guiding element 24 such that in the storage position of the injection device 1 the needle end 22 is arranged spaced apart from the cartridge seal 26. Thus firstly access to the inner chamber of the cartridge 3 to the medicine 14 is prevented. Furthermore, in the storage position of the injection device 1 both needle ends 21, 22 are arranged inside the support housing 2 and thus needle stick injuries are prevented. Furthermore, as explained in more detail in the following, the entire needle arrangement 6 is kept in a completely sterile state during the entire storage period prior to the specified use of administering the medicine 14.

The needle protection element 7 (needle cover), which is in active connection with the second drive unit 8 (needle cover spring), can be shifted by means of the latter from a non-effective position into a position covering the needle end 21, which projects after the injection procedure over the distal end 11 of the support housing 2. The triggering of the second drive unit 8 and the displacement of the needle protection element 7 are also described in detail in the following. The needle protection element 7 together with the second drive unit 8 is arranged in the region of the exterior of the support housing 2 and is supported at least partly on the latter.

The support housing 2 is also surrounded over the most part of its longitudinal extension between the distal end 11 and the proximal end 12 by the activating sleeve 9 (outer housing) described above and is mounted in the latter. The support housing 2 and the activating sleeve 9 are comprised in a general housing. In this case only the distal end 11 of the support housing 2 projects over the activating sleeve 9 in axial direction. Here the term "over the most part" of its longitudinal extension is defined such that the activating sleeve 9 extends in relation to the length of the support housing 2 over an longitudinal extension in a lower limit of at least 50% and an upper limit of up to 100%. In this case advantageous values of the longitudinal extension are at least 50%, preferably at least 60%, in particular at least 70%, preferably at least 80%, preferably at least 90%, particularly preferably at least 95%. As almost the entire support housing 2 is mounted by the activating sleeve 9 or arranged inside the latter the needle protection element 7 is arranged with the second drive unit 8 interacting therewith, as viewed in axial section, radially between the support housing 2 and the activating sleeve 9. In this way there can be no influence on the second drive unit 8 for its triggering or deactivation. The activating sleeve 9 can also be defined as a triggering (or actuating) sleeve. Furthermore, the latter is used not only for the function of actuating or triggering the first drive unit 4 but also for the user to hold the entire injection device 1 and keep holding it in the same way during the whole administration process.

The support housing 2 comprises in turn a front and a rear support housing part 27, 28 (cartridge container), whereby the front support housing part 27 faces the distal end 11 and thus the patient 10. The rear support housing part 28 is arranged closer to the proximal end 12. The two support housing parts 27, 28 delimit and define respectively a front and rear holding chamber 29, 30, and can be coupled together in a connecting section 31 arranged between the latter by a coupling device 32 in the direction of the longitudinal axis 13.

The coupling device 32 has on the two support housing parts 27, 28 cooperating locking elements, which are designed such that the two support housing parts 27, 28 are locked.

In the region of the distal end 11 the support housing 2 or the front support housing part 27 has an opening 35 allowing the passage of the needle end 21 of the needle arrangement 6. In this opening 35 a penetrable sealing stopper 36 is arranged in a position sealing the front holding chamber 25 relative to the outer environment.

The front holding chamber 29 has the needle arrangement 6 arranged therein. The connecting section 31 gripping over the rear support housing part 28 ends with a wall part 38 springing back to the longitudinal axis 13, which is preferably arranged in a plane aligned perpendicular to the longitudinal axis 13. Said wall part 38 has a face end 39 facing the rear support housing part 28, which is also arranged preferably in the plane aligned perpendicular to the longitudinal axis 13. On the wall part 38 also on the side averted from the rear support housing part 28 the second drive unit 8 is supported with a further driving means 40 (needle cover spring). The driving means 40 can in turn be formed by a pretensioned compression spring or similar spring element.

Furthermore, on the backspringing face end wall 39 of the wall part 38, a shoulder 41 designed to be wedge-shaped in axial cross section and continuous around the circumference can be arranged. The wedge-shaped tapering is in this case aligned in the direction of the rear support housing part 28.

On the rear support housing part 28 at its end facing the front support housing part 27 a sealing element 43 designed to be continuous around the circumference is arranged or secured thereon. The sealing element 43 is preferably arranged on a face end side of the rear support housing part 28 and secured there. The sealing element 43 designed to be circumferential bears both against the external surface of the cartridge 3 and an internal surface of the front support housing part 27, in particular in the connecting section 31. This bearing preferably seals around the entire circumference on both surfaces.

The front support housing part 27 comprises a casing 46 designed to be roughly cylindrical, which in the region of the distal end 11 comprises the opening 35 described above, which is sealed by the sealing stopper 36. The casing 46 is continuous and thus designed to seal up to the connecting section 31.

The sealing element 43 bears in a sealing manner against the face end wall 39 of the wall part 38 or the shoulder 41 arranged thereon. To obtain a better peripheral seal, the wedge-shaped shoulder 41 described above is provided, which pushes in axial direction into the sealing element 43 during its bearing thereon.

The front holding space 29 is completely sealed. Furthermore, the peripheral sealing element 43 can also be used as a damping holder for the cartridge 3 with the medicine mounted in the support housing 2. In this way impact and stress from the external activating sleeve 9 towards the cartridge 3 with the medicine 14 can be damped or completely reduced and absorbed.

Figure 3:
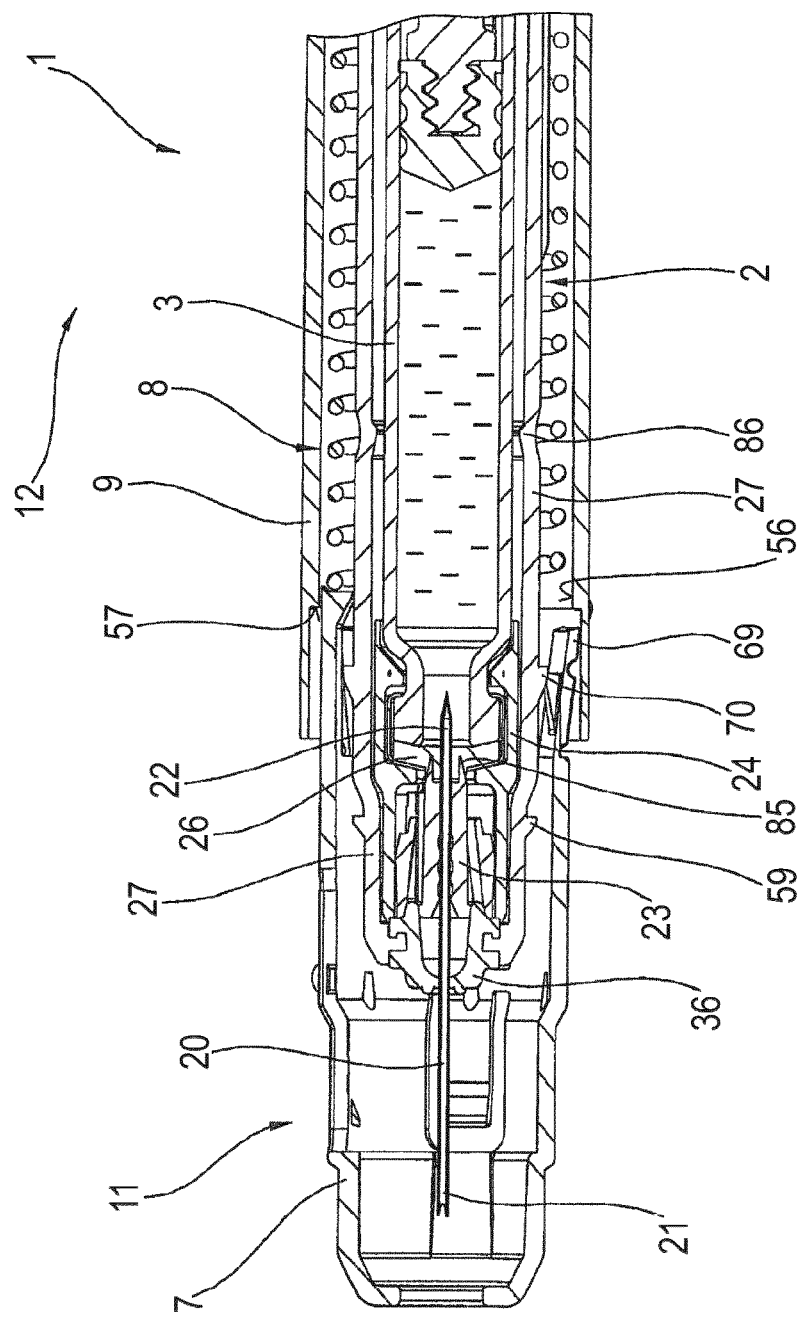
FIG. 3 shows the injection device according to FIG. 1 in a position of the needle protection element covering the cannula, in axial cross section and a simplified representation.

A further damping device 86 can be seen in FIG. 3. This is formed on the internal surface of the support housing 2, in particular the front support housing part 27, as a flange projecting into the clear cross section or as a constriction of the casing 46. The arrangement is as viewed in axial direction in the region or section of the needle support 23 or the guiding element 24. In a drop test the cartridge 3 or the needle support 23 and/or the guiding element 24 could thus be supported thereon and an unintentional further movement of the cartridge 3 in the direction of the distal end 11 could be stopped. The damping device 86 thus forms a mechanical resistance against an axial movement.

The activating sleeve 9 is designed at its proximal end 12 such that the latter is used for mounting or coupling the safety cap 18. For this a sleeve wall 47 of the largely cylindrical or tubular activating sleeve 9 in the region of its proximal end 12 has a thinner wall and thus forms a mounting area on the outside of the sleeve wall 47. A cap casing 49 grips over a mounting area on the side facing away from the longitudinal axis 13 and is thus preferably designed to run flat relative to the exterior of the sleeve wall 47.

Figure 5:
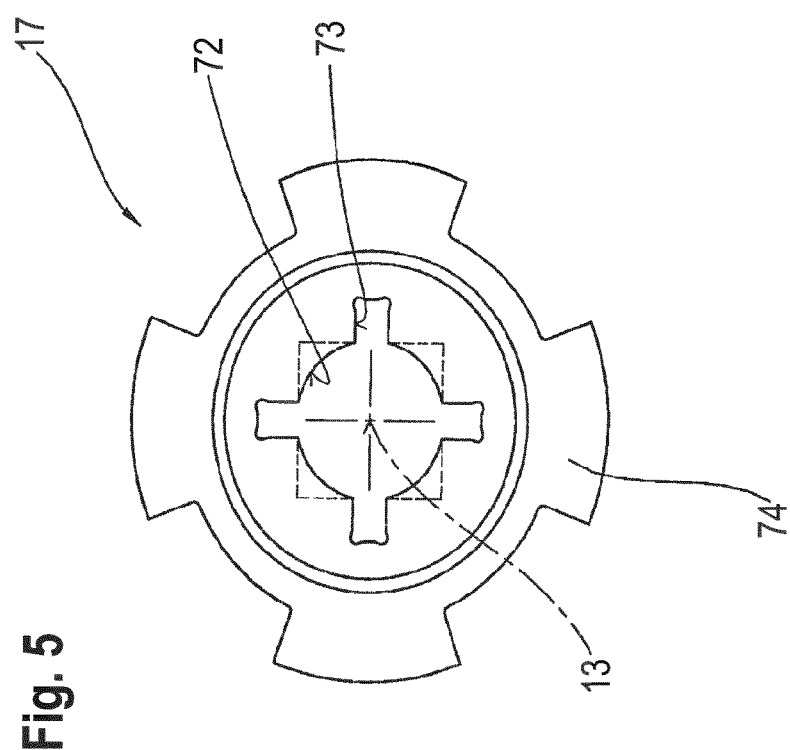
FIG. 5 shows the holding disc of the in plan view and in a simplified representation.

Furthermore, the activating sleeve 9 at its proximal end 12 in the region of the longitudinal axis 13 has at least one wedge-shaped activating element 50. Said activating element 50 can be designed to be continuous over the circumference and on the side facing the drive unit 4 has a conical surface 51 tapering to the side averted from the drive unit 4. After removing the safety cap 18 with its safety pin 19 upon a relative displacement of the activating sleeve 9 relative to the support housing 2 it is possible to displace the ends of the holding arms 16 on either side of the conical surface 51 radially inwards—i.e. in the direction of the longitudinal axis 13, and in this way release the holding disc 17 (FIG. 5). This release process with such injection devices 1 and is known to the skilled person in the present technical field. A description and citation of various such release mechanisms to which the present invention could be applied are provided in the background section above.

In FIG. 1, the front holding chamber 29 and the cannula 20 coming later into connection or contact with the patient 10 for the injection and the associated administration of the medicine 14 is in a completely sterilised state. Furthermore, in the region of the proximal end 12 of the injection device 1 a detent device 52 is shown in a simplified form, which causes a locking effect between the support housing 2, in particular the rear support housing part 28 and the activating sleeve 9.

Thus the rear support housing part 28 has on its external surface and in the region of the proximal end 12 at least two detent noses 53, 54 spaced apart from one another in the direction of the longitudinal axis 13, which cooperate with a detent element 55 arranged on the activating sleeve 9 in two different longitudinal positions. The detent element 55 formed on the activating sleeve 9 is preferably a component of the sleeve wall 47 and can for example be connected to a resilient detent arm or formed by the latter. The first detent nose 53 is thus arranged closer to the proximal end 12 than the other detent nose 54. The spacing of the two detent noses 53, 54 corresponds preferably to the triggering movement of the activating sleeve 9 relative to the support housing 2, which is necessary to release at least the first drive unit 4 and thus activate the injection procedure. The two detent noses 53, 54 define the relative positions of the support housing 2 with respect to the activating sleeve 9 on the one hand in the storage position and on the other hand in the injection position. Thus only a relative longitudinal displacement of the activating sleeve 9 with respect to the support housing 2 is possible from the storage position to the injection position, but a relative longitudinal adjustment in the opposite position is reliably prevented.

The actuation or triggering of the injection device 1 for the injection process from the storage position to the injection position is performed in that the entire injection device 1 is held by the hand of a user on the activating sleeve 9 (outer housing) and then the safety cap 18 is removed from the proximal end 12 of the activating sleeve 9. Thus the injection device 1 is activated for triggering (ready for actuation, but not yet actuated) and the following injection process. Subsequently, the entire injection device 1 with its distal or front end 11 is positioned on the point of the patient 10 where the medicine 14 is to be administered. In this way, the distal end of the needle protection element 7 and if necessary the sealing stopper 36 arranged on the front support housing part 27 in the opening 35 is supported thereon. By displacing the activating sleeve 9 in the direction of the distal end 11 and thus towards the patient 10, by the support of the support housing 2 on the body part of the patient 10, there is a relative displacement of the activating sleeve 9 in relation to the support housing 2. In this way, as already described above, the first drive unit 4, in particular the locked holding arms 16, is displaced by the activating element 50 radially inwards and in this way the locking with the holding disc 17 is released.

The relative axial displacement movement causes the resilient detent element 55 to disengage from the first detent nose 53, slide over the second detent nose 54 and afterwards support itself on this second detent nose 54. In this way the support housing 2 is held fixed in position relative to the activating sleeve 9. This locking is achieved in both axial directions, whereby the first support is performed between the holding arms 16 and the activating element 50 and the second support between the second detent nose 54 and the detent element 55.

Furthermore, the activating sleeve 9 in the region of the distal end 11 and on its internal surface 56 has a stop surface 57 (FIG. 3), which is preferably aligned perpendicular to the longitudinal axis 13. Said stop surface 57 can preferably be designed or arranged continuously over the inner circumference of the activating sleeve 9 and is preferably formed by a cylindrical or tubular recess in the sleeve wall 47.

Also the needle protection element 7 is secured under pretensioning of the second drive unit 8 relative to the support housing 2, in particular the front support housing part 27 in the storage position. This relative and detachable securing can best be seen in FIGS. 1, 3 and 4 in the region of the distal end 11. The support housing 2 or the front support housing part 27 has at its distal end 11 on its external surface a preferably continuous stop element 59. On the needle protection element 7 corresponding thereto at least one rocker-like lever element 60 is provided, which in the direction of the longitudinal axis 13 comprises spaced apart lever ends 61, 62. The lever end 61 lying closer to the distal end 11 is supported in the storage position of the injection device 1 on the previously described stop element 59 of the front support housing part 27 of the support housing 2. The additional lever end 62 projects into the recess of the activating sleeve 9 described above and in the direction of the stop surface 57. Depending on the selected spacing between the lever end 63 and the stop surface 57 the triggering time described in more detail below for the needle protection element 7 or the second drive unit 8 cooperating therewith can be varied. The second drive unit 8 with its resilient driving means 40 is supported in the region of its end section facing the proximal end 12 on the backspringing wall part 38. Furthermore, the second drive unit 8, in particular the driving means 40, is supported by its end section facing the distal end 11 on a face side of the needle protection element 7 facing the proximal end 12. In this way the driving means 40 of the second drive unit 8 is arranged on the one hand, as viewed in radial direction, between the support housing 2 and the activating sleeve 9 and on the other hand, as viewed in axial direction, on the backspringing wall part 38 of the support housing 2 and the face side of the needle protection element 7. By means of the support on the face side of the needle protection element 7 the driving means 40 of the second drive unit 8, as viewed in axial direction, is arranged behind the needle protection element 7 and thus on the side facing the proximal end 12 or the end section formed there. In this way on the needle protection element 7 it generates a pressing force directed towards the distal end 11. This pressing force is transferred from the needle protection element 7 via the lever element 60 arranged or formed thereon to the stop element 59 arranged on the support housing 2 and is thus supported there.

As already described above, the entire needle arrangement 6, in particular the cannula 20 is arranged with its needle end 22 facing the cartridge seal 26 spaced apart from the latter in the storage position. Furthermore, the needle support 23 is held axially displaceably in the guiding element 24 or mounted therein, whereby in the storage position the needle support 23 is secured by at least one detachable holding element 63 relative to the guiding element 24. This can best be seen from the view of FIG. 6.

As can be seen better from FIG. 1 an adjusting cam 64 is allocated to the holding element 63 of the needle support 23 or arranged thereon, which adjusting cam projects over the needle support 23 on the side averted from the longitudinal axis 13. The front support housing part 27 of the support housing 2 in this section has an internal clear dimension or a cross section which is designed to be approximately cylindrical and thereby the adjusting cam 64 is arranged immediately adjacent thereto until bearing lightly against an inner wall 65 of the sleeve-like support housing part 27. If now by means of the first drive unit 4 the cartridge 3 together with needle arrangement 6 is moved in the direction of the distal end 11, firstly the needle end 21 facing the distal end 11 sticks through the sealing stopper 36 arranged in the opening 35 of the front support housing part 27 and then enters directly into the surface section of the patient 10 provided for the administration.

Figure 4:
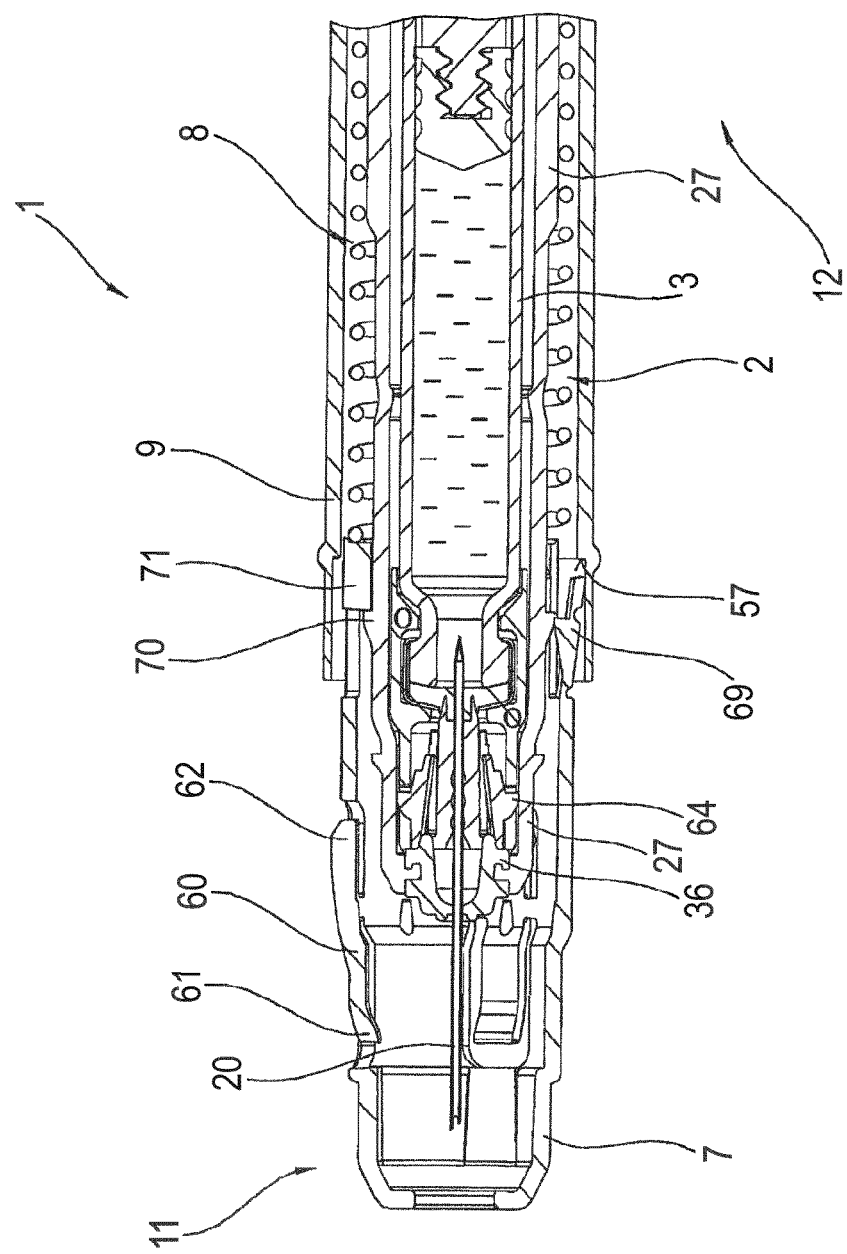
FIG. 4 shows the injection device according to FIG. 3, but in a different cross sectional plane.

The activated and inserted position of the cannula 20 into the patient 10 can best be seen from FIG. 4. In this case the cartridge 3 together with the needle arrangement 6 has been shifted in the direction of the distal end 11. Furthermore, in the region of the distal end 11 on the internal wall 65 of the front support housing part 27 a control cam 66 projecting in the direction of the longitudinal axis 13 is formed, which for example is formed by a narrowing of the wall part forming the front support housing part 27. Likewise the formation of a rib or web on the internal wall 65 would be possible. The control cam 66, which is offset in the direction of the longitudinal axis 13, with the associated reduction or narrowing in the cross section, comes into engagement with the adjusting cam 64 during the displacement movement of the needle arrangement 6, and is shifted together with the holding element 63 radially inwards in the direction of the longitudinal axis 13. By means of this displacement the holding element 63 is disconnected from the guiding element 24. Because of this release and the mechanical bearing of the needle support 23 on the sealing stopper 36 arranged at the distal end 11, there is a further relative displacement between the needle support 23 and the guiding element 24. By means of this relative displacement the needle end 22 facing the proximal end 12 penetrates the cartridge seal 26, whereby a flow connection is now created between the inner chamber of the cartridge 3 via the cannula 20 to the insertion point into the patient 10. By means of the mechanical stop of the needle support 23 against the sealing stopper 36 and the completion of the relative displacement between the needle support 23 and the guiding element 24, also the cartridge 3 is secured fixed to the support housing 2. The sealing stopper 36 is thus designed at the end facing the needle support 23 or the guiding element 24, such that the latter also performs a damping function for completing the adjusting movement and cartridge 3 mostly made of glass does not get broken by the sudden displacement movement and the associated impact at the distal end 11. Therefore, a preferably circumferential flange projects from the opening 35 in the direction of the front holding chamber 29, which thereby comes into contact with the needle arrangement 6.

By means of the further pressure effect or force loading of the drive unit 4 in the direction of the distal end 11 a cartridge stopper 68 arranged on a piston rod 67 is pushed into the inner chamber of the cartridge 3 and thus injects the medicine 14 via the cannula 20 injected at this time into the patient 10.

During the relative displacement of the activating sleeve 9 relative to the support housing 2 and the associated triggering of the first drive unit 4 the second lever end 62 of the lever element 60 (first locking mechanism) facing the proximal end 12 comes into contact with the stop surface 57 formed on the internal surface 56 of the activating sleeve 9. In this way the lever end 62 facing the proximal end 12 is pivoted radially in the direction of the longitudinal axis 13. Then the rocker-like mounting of the lever element 60 causes the first lever end 61 of the lever element 60 facing the distal end 11 to disengage from the stop element 59 by a radial pivoting to the side averted from the longitudinal axis 13. Thus the support of the needle protection element 7 on the support housing 2, in particular the front support housing part 27, is released, and simultaneously the second drive unit 8 is activated. In this way, after the completion of the injection procedure and the removal of the injection device 1 from the patient 10 immediately the needle protection element 7 with the drive unit 8 cooperating therewith is shifted from its non-effective position (retracted) into the position (extended) covering the needle end projecting after the injection procedure over the distal end of the support housing 2. It is advantageous, if with the axial displacement of the activating sleeve 9 relative to the support housing 2 the release of both the first and second drive units 4, 8 is performed simultaneously.

FIG. 3 shows the protected position of the cannula 20 after the injection procedure and the removal from the injection site on the patient inside the needle protection element 7.

In order to prevent the unintentional restoring of the needle protection element 7 from the protecting and covering position to a new release position of the needle end 21, the needle protection element 7 also has at its proximal end 12 at least one elastically deformable safety element 69 (second locking mechanism), which can be designed as an elastically deformable lever. The needle protection element 7 is shifted during its relative displacement relative to the support housing 2 into the position covering the needle arrangement 6 by the drive unit 8. The restoring of the needle protection element 7 in the direction of the proximal end 12 is prevented by the support of the safety element 69 on the stop surface 57 formed on the internal surface 56 of the activating sleeve 9. In this case the needle protection element 7 is displaced by means of the second drive unit 8 via a predefined displacement movement up to a mechanical stop. The safety element 69 thus projects in this case into the free space in front of the stop surface 57. Furthermore, the safety element 69 can be arranged at a specific distance in front of the stop surface 57 or also immediately adjacent thereto. The locking position of the safety element 69 is additionally supported or secured in the position of the needle protection element 7 covering the needle arrangement 6 by an adjusting element 70 arranged on the support housing 2. The adjusting element 70 can be designed as a circumferential web-like shoulder on the support housing 2 or the front support housing part 27, whereby the adjusting element 70 during the relative displacement of the needle protection element 7 pushes or moves the safety element 69 radially to the side averted from the longitudinal axis 13 relative to the support housing 2. By means of this mechanical locking of the safety element 69 onto the stop surface 57 and the radial pretensioning by the adjusting element 70 a secured covering of the cannula 20 by the needle protection element 7 is ensured.

The axial adjustment movement of the needle protection element 7 relative to the support housing 2 can be ended by a positive stop between a detent element 71 arranged on the proximal end 12 and the adjusting element 70 arranged on the support housing 2 in the direction of the distal end 11. In this way the needle protection element 7 is adjusted by a predefined adjustment movement in the direction of the distal end 11, whereby in this position the cannula 20 of the needle arrangement 6 is completely covered. This can best be taken from FIG. 6.

Furthermore, it can also be taken from FIG. 3 that the needle support 23 on its side facing the cartridge seal 26 comprises a sealing shoulder 85 which completely surrounds the cannula 20 at a predeterminable radial distance and projects in axial direction. This shoulder is designed, as viewed in axial cross section, to taper wedge-like in the direction of the cartridge seal 26. On penetrating the cartridge seal 26 with the cannula 20 there may be leakages in the immediate penetration area between the cannula 20 and the cartridge seal 26. The seal is then produced by the sealing shoulder 85 in cooperation with the elastically deformable cartridge seal 26, as the sealing shoulder 85 penetrates into the material and also pushes the latter against cannula 20.

FIG. 5 shows the holding disc 17 of the safety device 5 in a plan view and in a simplified representation. Thus the holding disc 17 in its centre has a preferably round opening 72 as well as recesses 73 adjoining the latter and extending radially outwards. Independently of this it would also be possible to make the cross section of the throughput 72 polygonal, in particular quadratic, as indicated by dashed lines. The number of recesses 73 thus corresponds to the number of holding arms 16 of the first drive unit 4 to be secured in the storage position. In the present exemplary embodiment four holding arms 16 are provided evenly distributed over the circumference, whereby for better positioning, guiding and mounting of the holding arms 16 in the holding disc 17 recesses 73 are provided. Furthermore, the holding disc 17 on its external circumference has additional segment-like shoulders 74. Said shoulders 74 are used for connecting the holding disc 17 to the rear support housing part 28 of the support housing 2. This can be for example in the form of a snap or detent connection.

The administration of the medicine 14 supplied in the cartridge 3 can be performed in the following manner. The two drive units 4, 8 are held secured in their pretensioned position inside the injection device 1, whereby the front holding chamber 29 together with the entire needle arrangement 6 is in a sterile state. If the injection is now to be administered, firstly by removing the safety device 5, i.e. the safety cap 18 together with the safety pin 19, the first drive unit 4 is released from an actuation locked state to an actuation ready state. The user holds the entire injection device 1 on the activating sleeve 9 and places the latter with its distal end 11 on the body part of the patient 10 to receive the medicine 14. In this way the support of the support housing 2 together with the needle protection element 7 arranged thereon on the surface of the patient 10 is achieved.

By means of the axial adjustment movement of the activating sleeve 9 in the direction of the distal end 11, the first drive unit 4 is triggered or activated, whereby the cartridge 3 together with the needle arrangement 6 is adjusted automatically in the direction of the distal end 11. During this axial adjustment movement additionally the needle support 23 together with the cannula 20 is released from the locked first position on the guiding element 24 and the needle end 22 is penetrated through the cartridge seal 26. Prior to this penetration the needle end 21 facing the distal end 11 has already been pushed into the patient 10, whereby the flow connection between the needle end 22 averted therefrom with the internal chamber of the cartridge 3 is performed immediately afterwards. Immediately afterwards or also simultaneously with the axial displacement of the activating sleeve 9 also the second drive unit 8 is triggered for the movement of the needle protection element 7. By means of the first drive unit 4 the medicine 14 is the administered to the patient 10. After completing the administration the entire injection device 1 is removed from the patient 10. By means of the already activated or triggered second drive unit 8 during the removal of the injection device 1 from the patient 10 the needle protection element 7 is adjusted until the cannula 20 is mounted completely therein or the detent part 71 of the needle protection element 7 comes to bear against the adjusting element 70. At the same time as the complete axial displacement of the needle protection element 7 into the covering position the latter is hindered by means of the safety element 69 by supporting on the stop surface 57 against a repeat restoring into a release position of the needle end 21.

Figure 6:
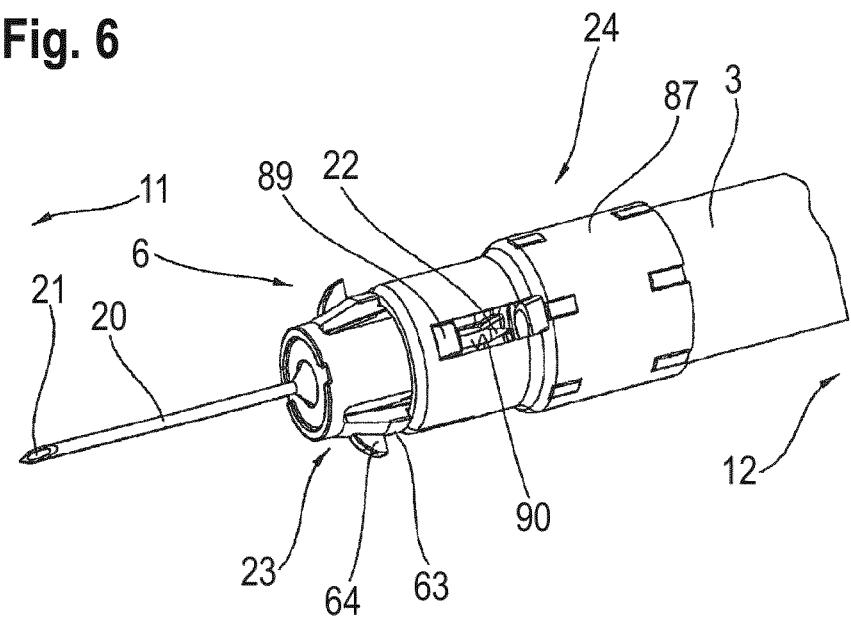
FIG. 6 shows the needle arrangement in the coupled position on the cartridge according to FIGS. 1 to 5, in a simplified view.
Figure 7:
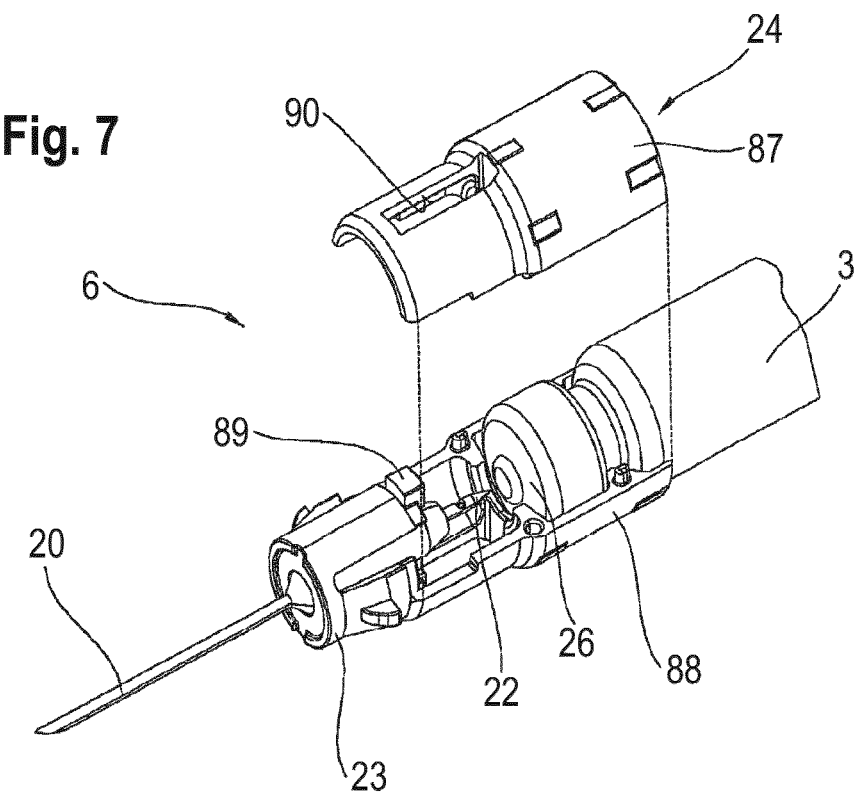
FIG. 7 shows the needle arrangement according to FIG. 6 with a raised guiding element of the guide element, in a simplified view.

In FIGS. 6 and 7, the needle support 23 and the cannula 20 mounted and held therein is mounted jointly in the guiding element in axial direction displaceable lengthways relative to said guiding element 24. FIG. 6 also shows the support of the holding element 63 on the guiding element 24. On the holding element 63 the previously described adjusting cam 64 is arranged, which on the axial displacement of the cartridge 3 together with the guiding element 24 and the needle support 23 releases the lock and thus the injection process of the needle end 22 into the cartridge seal 26 is performed.

The guiding element 24 is formed in this embodiment shown here from two guiding elements 87, 88, which can be joined together like half-shells to form the tubular guiding element 24.

By means of the raised position shown in FIG. 7 of the guiding part 87 lying at the top here the spaced apart position of the needle end 22 from the cartridge seal 26 can easily be seen. Furthermore, the needle support 23 preferably has diametrically opposite guiding shoulders 89, which engage into a guiding slot 90 in the guiding part 87 and/or 88.

In the mounted position shown in FIG. 6 of the guiding element 24 the needle support 23 is held fixed in both axial directions relative to the guiding element 24. The guiding shoulder(s) 89 delimit in cooperation with the guiding slot 90 the adjustment movement of the needle support 23 in the direction of the distal end 11. The holding element(s) 63 however prevent an axial displacement of the needle support 23 in the direction of the proximal end 12 up to its release by the interaction of the adjusting cam 64 with the control cam 66 of the support housing 2. The relative axial displacement movement of the needle support 23 in the direction of the proximal end 12 and the thus associated penetration of the needle end 22 through the cartridge seal 26 can be delimited by the selected longitudinal extension of the guiding slot 90.

The two guiding elements 87, 88, designed here as half-shell parts, are prevented from falling out in the assembled state by the bearing thereof against the internal surface of the support housing 2 in particular the front support housing part 27. In this way a simple assembly is achieved with a good connection. Furthermore, a mutual locking of the two guiding parts 87, 88 is possible by an offset arrangement of pins and pin mounts.

This axial guiding has the advantage that also an axial injection movement of the cannula 20 relative to the longitudinal axis 13 is performed into the tissue of the patient 10 or user.

Figure 8:
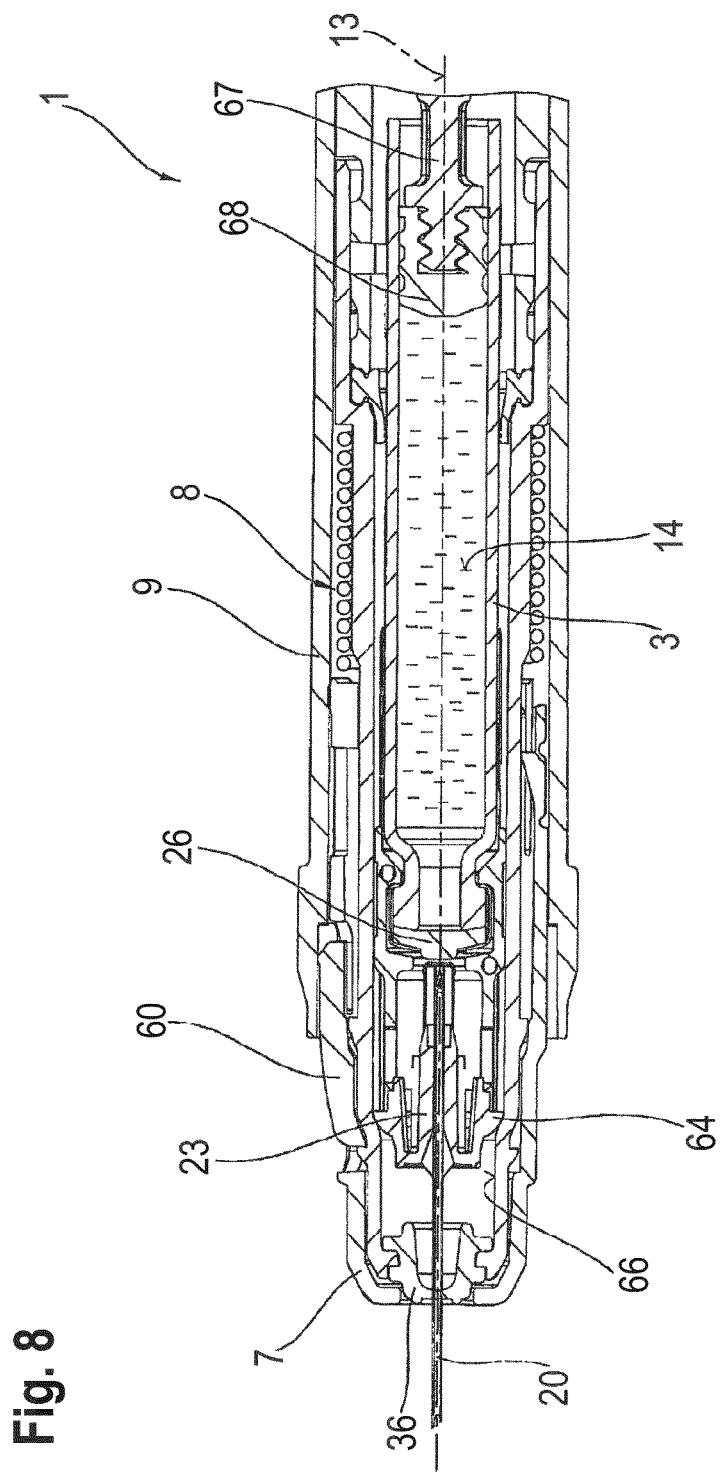
FIG. 8 shows the needle arrangement in the coupled position on the cartridge according to FIGS. 1 to 7 during the adjustment movement for administering the medicine in a position immediately prior to the cooperation of the adjusting cam with the control curve, in axial cross section.

FIG. 8 shows the already described in detail interaction of the control cam 66 of the support housing 2, in the present exemplary embodiment of the front support hosing part 27, with the adjusting cam 64 arranged on the holding element 63 in an enlarged view.

This results in the radial displacement and the associated release of the locking between the holding element 63 and the guiding element 24. Depending on the position of the control cam 66, as viewed in axial direction, also the release for the injection movement of the needle end 22 into the cartridge seal 26 can be determined. The earlier the release takes place the sooner the cartridge 20 is in flow connection with the inner chamber of the cartridge 3 containing the medicine 14.

Figure 9:
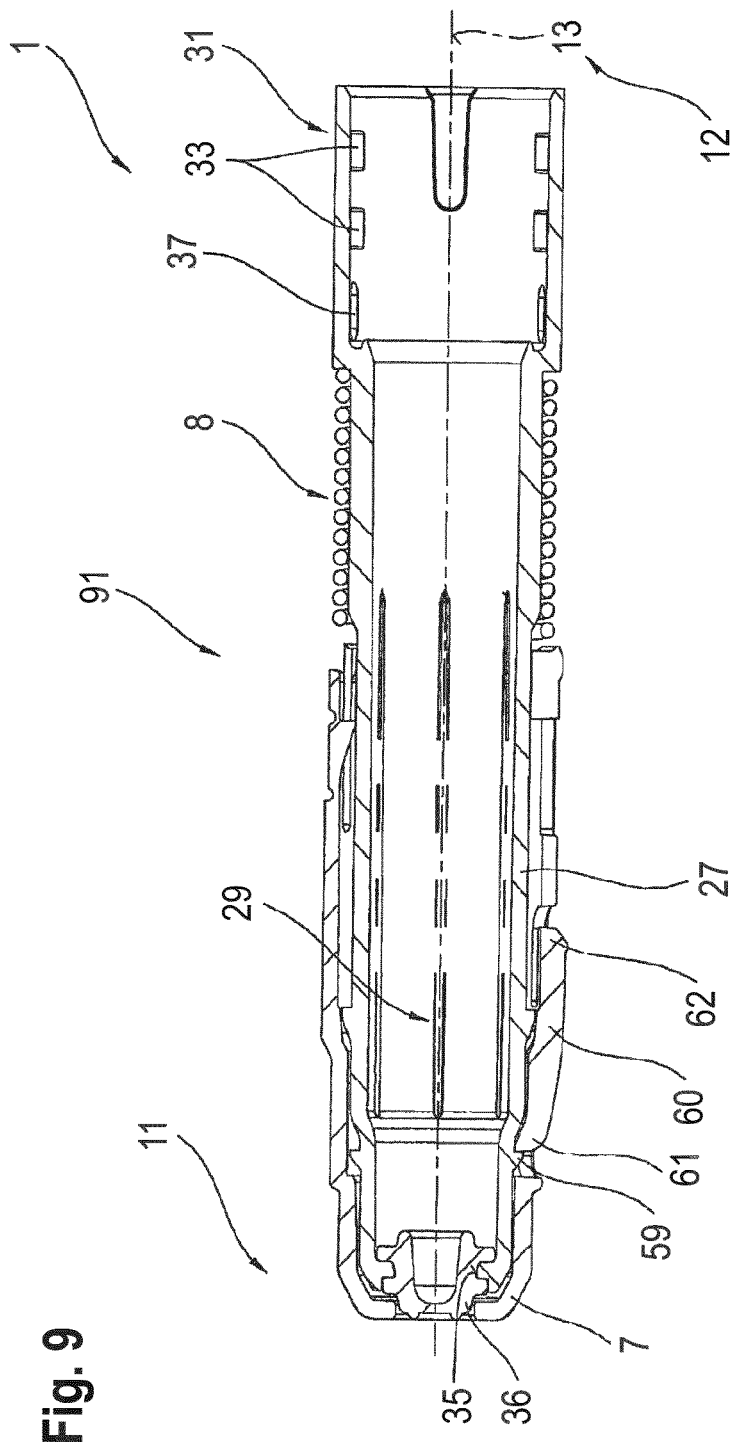
FIG. 9 shows a first premounted component group of the injection device in the region of the front support housing part, in axial cross section.
Figure 10:
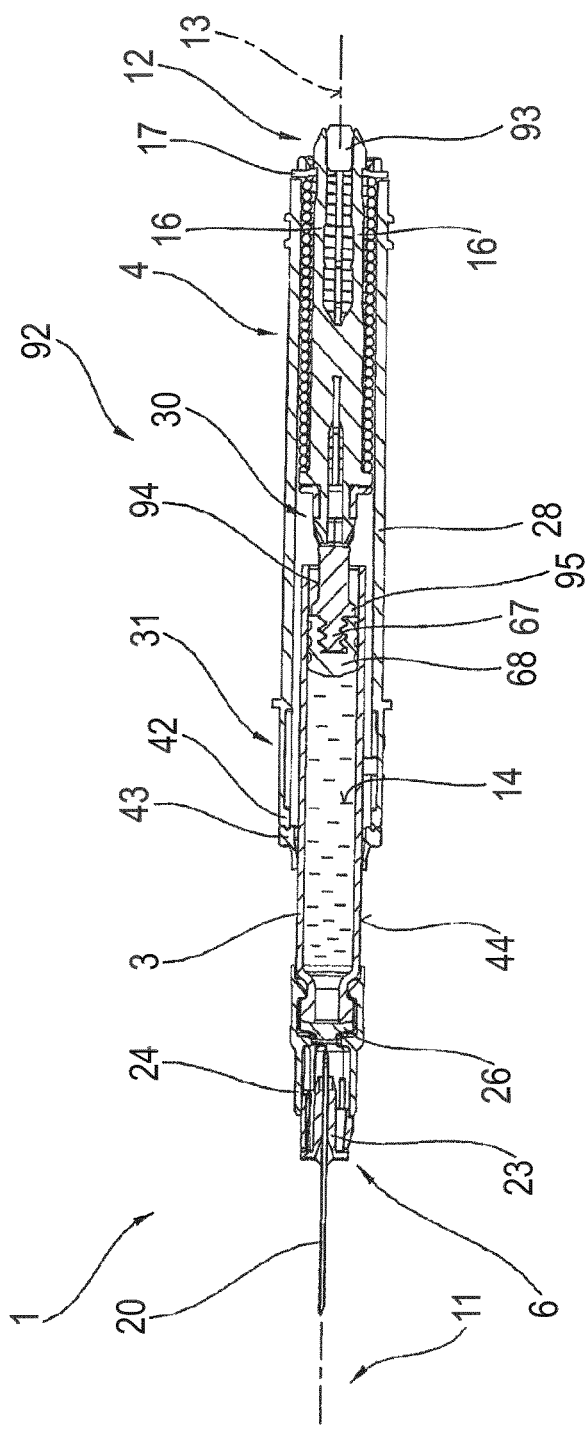
FIG. 10 shows a second premounted component group of the injection device in the region of the rear support housing part, in axial cross section.

Referring to FIGS. 9 and 10, the individual components forming the injection device 1 are designed such that the latter can be assembled or preassembled into component groups or units 91, 92. In a subsequent additional assembly stage then the two component units 91, 92 are joined together with the remaining components, as shown in FIG. 1

Thus a first component 91 in the region of the distal end 11 of the injection device 1 comprises the front support housing part 27, the sealing stopper 36 and the needle protection element 7 adjustable with the second drive unit 8. The needle protection element 7 is supported and locked in turn by the previously described lever element 60 on the stop element 59 of the front support housing part 27. The second drive unit 8, which is formed here by a spiral compression spring, is supported on the one hand on the step-like connecting section 31 of the front support housing part 27 and on the other hand on a face side of the needle protection element 7 facing the proximal end 12. By means of the pretensioned drive unit 8 according to the already described release of the lever element 60 the axial adjustment of the needle protection element 7 can be performed into the position covering the needle or the cartridge 20.

The second component 92 in the region of the proximal end 12 of the injection device 1 comprises in turn the rear support housing part 28, the first drive unit 4 mounted therein, the cartridge 3 with its cartridge stopper 26, the needle arrangement 6, the sealing element 43, the piston rod 67 with the cartridge stopper 68 and the holding arms 16, which can be held in position by means of the holding disc 17. In order to prevent the unintentional release of the first drive unit 4 by means of the disengagement of the holding arms 16 with the holding disc 17, it is shown a simplified manner in FIG. 10, that the holding arms 16 are held by a safety element 93 arranged in the region of the longitudinal axis 13 radially on the side facing away from the longitudinal axis 13. The safety element 93 is preferably designed to be cylindrical and is left so long on the component 92 until the final assembly with the component 91 and the activating sleeve 11 and the safety device 5 is performed.

In this way a high degree of prefabrication is achieved, whereby according to the desired medicine also the cartridge 3 can be connected to the needle arrangement 6 arranged thereon via the cartridge stopper 68 to the piston rod 67. The assembly of the cartridge 3 on the piston rod 67 can be performed as a function of the storage ability of the medicine 14.

In this way a simple method for assembling the injection device 1 can be created, in which firstly the previously described components 91, 92 are assembled together with all their individual parts and thus form a semi-finished product or intermediate product. In this way also there can be an external manufacture of the individual components and for example the preassembled components 91, 92 can be produced and assembled by different manufacturers. If during the assembly the first component 91 is joined to the second component 92 in the region of the connecting section 31 according to the position shown in FIG. 1, then said component group consisting of the two components 91, 92 is inserted into the activating sleeve 9. Prior to this or also after this then the preferably safety element 93 in the region of the holding arms 16 is removed and replaced by the cap-like safety device 5 with the safety pin 19. After this sterilisation can be performed in the inner chamber of the support housing 2, in particular in the region of the needle arrangement 6.

As already shown in FIG. 8, the piston rod 67 comprises a radial depression 94, which in the premounted position of the piston rod 67 on the cartridge 3 comes to bear or is arranged on the end of the cartridge 3 facing the proximal end 12. This reduction of the outer dimension, in particular the diameter of the piston rod 67 is performed in order over the entire storage period of the injection device with a possible pivoting of the cartridge 3 relative to the piston rod 67 to prevent damage to the cartridge 3 made mostly or preferably of glass at its proximal end. Thus the piston rod 67 is connected to the cartridge stopper 68. This can be performed preferably by a threaded arrangement. In the immediate bearing area of the piston rod 67 on the cartridge stopper the latter comprises a preferably flange-like shoulder 95. Said shoulder 95 is used for the mutual axial securing between the piston rod 67 and the cartridge stopper 68. The free position designed as a depression 94 of the piston rod 67 thus protects against damage during transport or in the case of unintentionally dropping the entire injection device 1. A further damping support of the cartridge 3 can be performed by the sealing element 43 on the rear support housing par 28, as already described above.

In the above, with reference to FIGS. 1 to 10, there has been provided a full description of one known kind of autoinjector to which the present invention could be applied. As has been explained, the prior art relied upon a a removable safety cap 18 comprising a safety pin 19. The safety pin is shown in an actuation locked state in FIG. 1 in which the injection device 1 is unable to be actuated, which is to state that the injection device 1 is locked against actuation. Thus, the user would not be able to axially displace the actuation sleeve 9 to actuate the injection device 1. Removal of the safety cap 18 would place the injection device in a safety released position in which the injection device 1 is ready or free for actuation. The actuation sleeve 9 may now be displaced to actuate the autoinjection process.

Removal of the safety cap 18 has, however, exposed a proximal or rear visage of the injector 1 as shown in FIG. 5. The proximal opening 72 in the holding disc 17 has been revealed, which could, for the reasons explained above, lead to confusion as to which end of the injection device 1 is the injection or needle end.

FIGS. 11 to 19 show a first embodiment of an injector 100 having a non-removable safety cap 102. That is, the safety cap 102 is configurable so that a safety pin 116 thereof is movable to the safety released position by non-removable operation of the safety cap 102. The injector 100 may be an injection device as described above with reference to FIGS. 1 to 10 or an autoinjector as described in EP2311510, U.S. Pat. No. 4,031,893, or U.S. Pat. No. 5,295,965 or the like.

Figure 11:
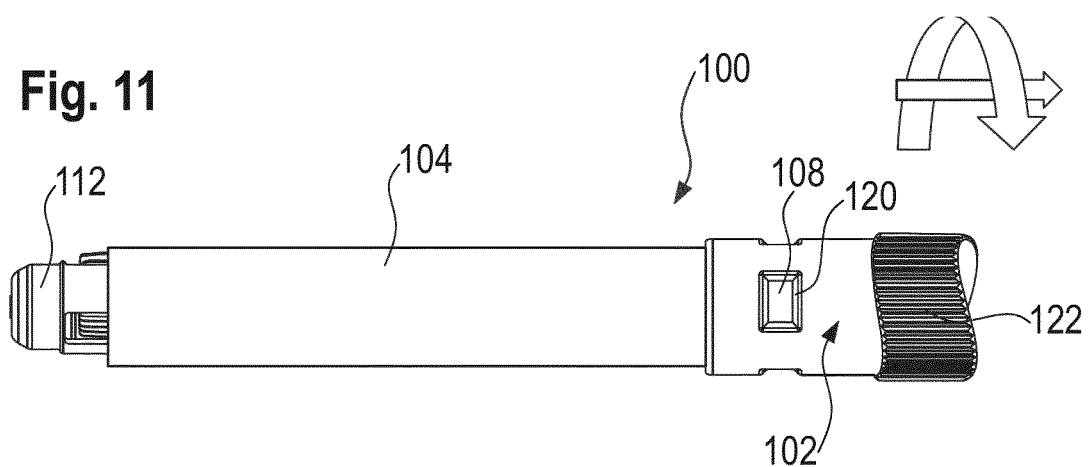
FIGS. 11 and 12 show an external view of an injector according to a first embodiment of the present invention. The injector has a safety cap moveable (by rotation in this embodiment) to affect axial movement of a safety pin from an actuation locked position as shown in FIG. 11 to a safety released position as shown in FIG. 12. One or more safety indicators are provided that are revealed upon movement of the safety cap to a position corresponding to the safety pin being in the safety released position. A rear end face of the safety cap provides a rear end face of the injector and is closed, i.e. without an opening, in an area of a central longitudinal axis of the injector.
Figure 12:
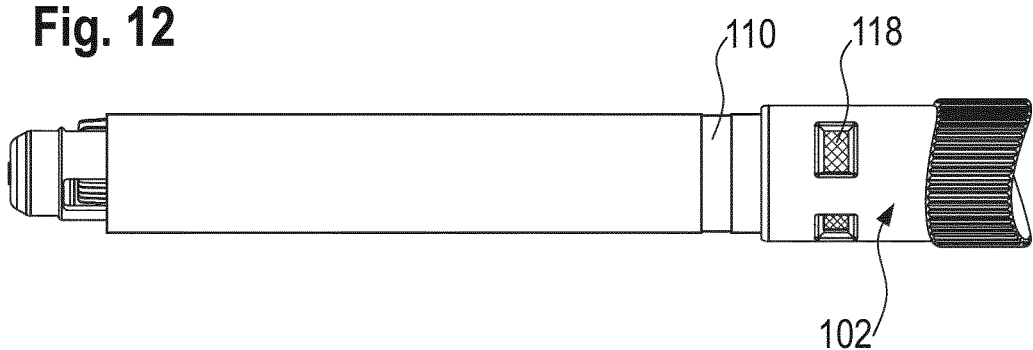
Figure 13:
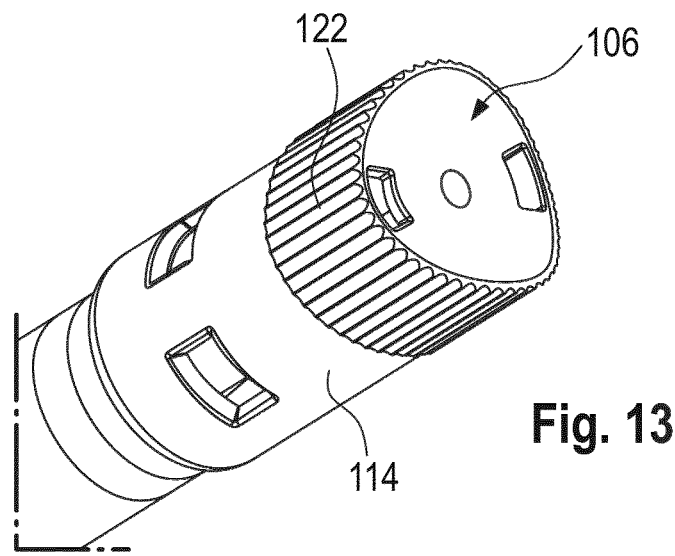
FIG. 13 shows a rear end view of the rear end face of the safety cap, which shows a dimple as a result of injection molding, but no opening. Further, the rear end face is undulated (e.g. wave-like) to make it clear that this is not the injection or needle end of the injector.

In FIGS. 11 to 13, there is shown an injector 100 having a safety cap 102. The safety cap 102 comprises a proximal or rear face 106 providing a rear cover portion and a sleeve formed body 114 providing a sleeve for mounting the safety cap 102 to an outer housing 104 of the injector 100. The outer housing 104 is comprised in a general housing of the injector 100. The proximal face 106 is mounted to a proximal or rear end of the outer housing 104 of the injector 100 so as to cover the proximal region of the outer housing 104. That is, the sleeve formed body 114 receives a proximal end region of the outer housing 104.

The proximal face 106 of the safety cap 102 thus forms the proximal face of the injector 100 as seen by the user. The proximal end face of the outer housing 104 is hidden by the safety cap 102.

The safety cap 102 includes a grip enhancing band 122 formed by longitudinally oriented ribs in this embodiment. This facilitates gripping by a user to rotate the safety cap 102. The rear or proximal face 106 is solid or closed in the most part. In particular, the rear or proximal face 106 does not comprise a through opening located at a centre thereof, i.e. at a location of a central longitudinal axis of the injector 100. This reduces likelihood of confusion as to which end of the injector 1 is the needle end (the end through which the needle protrudes during an injection operation). The proximal face 106 is unevenly formed by way of a wave shape forming a middle concavity between medial wave peaks, which further makes it clear that this is not the needle end of the injector 1.

The safety cap 102 is moveably mounted to the outer housing 104 so as to move along the outer housing 104 between a more distally disposed position as shown in FIG. 11 to a more proximally disposed position 102 as shown in FIG. 12. Thus, in this embodiment, the safety cap itself constitutes a rotatable part of the safety pin mover moveable between first and second positions corresponding to a safety pin 116 thereof (FIG. 17) being respectively in actuation locked and safety released positions. The safety cap 102 is rotatable by a user, which causes the safety cap 102 and its associated safety pin 116 to move proximally. This proximal movement is able to unlock a detent mechanism (discussed further below) so that the injector is ready for actuation. Prior to unlocking the detent mechanism, the injector 100 is locked against actuation.

The safety cap 102 is arranged to reveal one or more indicators 110, 118 upon moving from the more distally disposed position to the more proximally disposed position. That is, the safety cap 102 comprises a window 120 (plural windows in the shown embodiment), located on the sleeve body 114, that axially and rotationally move when the safety cap 102 moves between the positions to align with the indicator 118. Additionally or alternatively, a band 110 on the outer housing 104 is covered by the sleeve body 114 when the safety cap 102 is in the more distal position of FIG. 11 and is exposed when the safety cap 102 is in the more proximal position. The band 110 is visually distinct from neighbouring regions of the outer housing 104. Further, the window 120 reveals one colour in the safety cap position of FIG. 11 and a different colour in the safety cap position of FIG. 12. Other visual differentiators could be provided apart from colour, such as an icon, text, signs, etc. For example, an unlock icon could be used to indicate the safety released position of the safety pin 116 of the safety cap 102 in FIG. 12.

In use, the safety cap 102 is rotated by a user to move the safety pin 116 of the safety cap 102 from an actuation locked position as shown in FIG. 11, and in which the injector 100 is locked against actuation, to a safety released position as shown in FIG. 12, in which the injector 100 is able to be actuated. The safety cap 102 is merely moved along the outer housing 104, it is not removed therefrom so that a solid central region of the proximal face 106 of the safety cap 102 is always presented to the user. In fact, the safety cap 102 is engaged with the outer housing 104 in such a way (described further below) to prevent removal of the safety cap 102 from the outer housing 104 by a user. Thereafter, a needle or front end (112, which corresponds to a part of the needle cover exposed by the outer housing 104) is pressed against an injection site with the outer housing 104 grasped by the user. Pressure applied by the user will cause the outer housing 104 (or trigger sleeve as described above) to shift distally relative to internal components of the injector to actuate the injection operation (affecting an injection sequence in which a needle is extended, medicament is dispensed, and a needle cover is deployed and locked as described above). The safety cap 102 will reveal a different visual indicator 108, 118 in the more distal position of the safety cap 102 of FIG. 11, which corresponds to the actuation locked position of the safety pin 116 of FIG. 17, as compared to the visual indicator 108, 118 in the more proximal position of the safety cap 102 of FIG. 12, which corresponds to the safety released position of the safety pin 116.

Referring to FIGS. 14 to 17, nut and thread structure for the safety cap 102 is shown in detail. The safety cap 102 includes a protrusion 136 disposed to ride in a first helical groove 124 (which forms a thread that extends helically only part way around a circumference or periphery of the outer housing 104). The first helical groove 124 is formed in an outer surface of the outer housing 104. The protrusion 136 is located on an internal surface of the sleeve body 114 of the safety cap 102. The protrusion 136 rides or slides in the first helical groove 124 such that when a user turns the safety cap 102 about a longitudinal axis of the injector 100, the safety cap 102 moves axially to move the safety pin 116 between the actuation locked position of FIG. 11 and the safety released position of FIG. 12. In the present embodiment, safety cap 102 itself forms a rotatable part of a safety pin mover, and the helical groove 124 (which can also be described as a guide or thread) and the cooperating protrusion (cooperating structure) are also comprised in the safety pin mover).

The safety cap 102 comprises a stop surface 138 disposed adjacent the protrusion 136 on an internal surface of the sleeve body 114. The stop surface 138 protrudes from the internal surface of the sleeve body 114, but to a lesser extent than the protrusion 136. The outer housing 104 has a second, less deep helical groove 126 along which the stop surface 138 rides or slides. The second helical groove 126 starts with a first ridge 128 acting as a cooperating stop surface and ends with a second ridge 130. The stop surface 138 cooperates with the ridges 128, 130 to define start and end stop positions (or first and second stop positions) for movement of the safety cap 102 (which is itself the rotatable part of the safety pin mover in the present embodiment), specifically the protrusion 136 thereof, along the helical groove 124. The stop surface 138 is angled and the ridges 128,130 are angled, but a user noticeable force bump is required in order to move stop surface 128 past the respective ridges 128, 130. The cooperation of the stop surface 138 and the first and second ridges 128, 130 is such that the safety cap 102 does not move out of the start or end position unless forced to do so by a user turning the safety cap 102. The helical groove 124 becomes more circumferential in direction of extension at each end thereof (e.g. purely circumferentially extending) corresponding to the start and end positions.

The safety cap 102 comprises an installation channel 134 that extends axially. The safety cap 102, particularly the protrusion 136 thereof, is slid along the installation channel 134 during mounting of the safety cap 102. The installation channel 134 extends to the first helical groove 124. The installation channel 134 and the first helical groove 124 have a step 140 at their interface. The step 140 serves to prevent dismounting of the safety cap 102 from the outer housing 104. Specifically, the protrusion 136 moves distally along the installation channel 134 and passes over the step 140 to mount the safety cap 102 to the outer housing 104. The reverse axial movement to dismount the safety cap 102 is not possible because of a blocking interaction of the step 140 and the protrusion 136. The step 140 runs the length of the first helical groove 124 to form a holding surface that interfaces with the protrusion 136 forming a cooperating holding surfaces, which together prevent removal of the safety cap 102. Alternatively put, and referring to FIGS. 15 and 16, the protrusion 136 further forms a rearwardly facing surface of the safety cap 102 that interfaces with a forwardly facing surface of the first helical groove 124, thereby forming interfacing holding surfaces to prevent removal of the safety cap 102 from the outer housing 104 when the safety pin 116 is in the safety released position.

Figure 16:
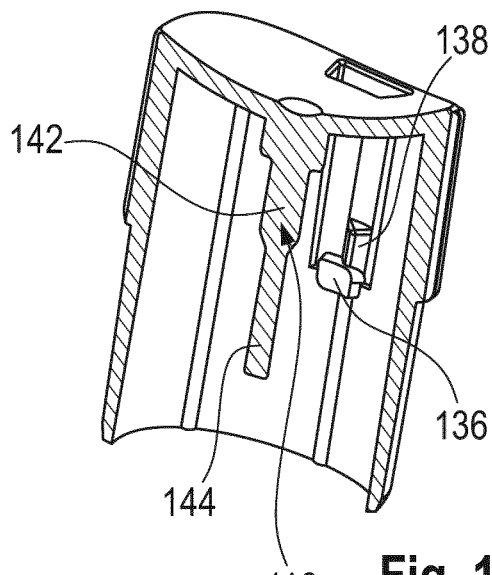
FIG. 16 shows a longitudinal cross-section of the safety cap revealing the inside thereof. In particular, the safety cap has an internal safety pin for locking against holding arms of the injector described above (or some other detent mechanism of another injector construction). There is shown a stop feature and protrusion, where the protrusion rides in the thread described above and the stop feature forms a stop surface of the safety cap for defining the start and stop positions.
Figure 17:
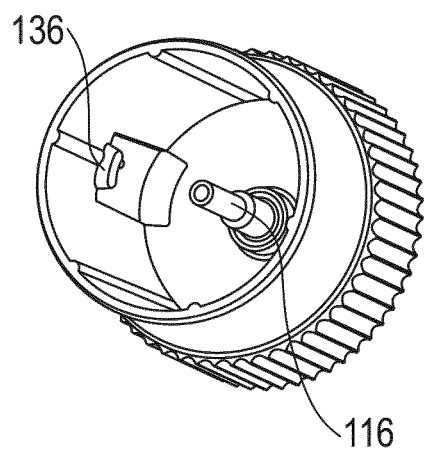
FIG. 17 shows the inside of the safety cap by viewing from the front side.

Referring to FIG. 16, the safety cap 102 has a centrally disposed (i.e. aligned with a central longitudinal axis of the injector 1) safety pin 116 depending from an internal surface of a rear end face or rear cover portion 106 of the safety cap 102. The safety pin 116 has a radially enlarged, axially extending region 142 and a radially thinned, axially extending region 144. The radially enlarged region 142 is rearwardly disposed to the radially thinned region 144. The safety pin 116 is to extend into a rear opening 132 in a rear end of the outer housing 104. The safety pin 116 extends through the rear opening 132 and into the opening 72 through the holding disc 17 shown in FIG. 5 of the present application. Referring to FIG. 1 of the present application, the safety pin 116 extends into an inner radial space between the holding arms 16. The holding arms 16 (or resilient arms) and the holding disc 17 form a detent mechanism that is disengageable to actuate an injection operation. When in the actuation locked position thereof as shown in FIG. 11, the enlarged region 142 prevents inward deflection of proximal ends of the holding arms 16 by blocking such, thereby preventing that the holding arms 16 could be disengaged from the holding disc 17 and thus preventing actuation of the injector 1. When the safety cap 102 is moved to a position corresponding to the safety released position of the safety pin 116 as shown in FIG. 12 by a user turning the safety cap 102 to move it proximally, the enlarged region 142 moves out from being between the holding arms 16 to free the holding arms 16 to be deflected inwardly to actuate the injector 1 by the holding arms 16 disengaging the disc 17. Although the thinned region 144 of the safety pin 116 remains radially and axially between the holding arms 16 (and extending through the opening 72 in the holding disc), the thinned region 144 does not block inward deflection of the holding arms 16.

The thinned region 144 of the safety pin 116 serves a guiding function for ensuring axial alignment of the safety pin 116 with the opening 132 in the outer housing 104 and also the opening 72 in the holding disc 17. It also serves an important function during manufacturing as can be understood from FIG. 10. In FIG. 10, component 92 is supplied with a safety element 93 preventing inward deflection of the holding arms 16 to prevent accidental actuation during assembly. When the safety cap 102 is assembled to the injector 1, the safety pin 116 moves the safety element 93 distally into a not active position (see FIG. 19) and is replaced by the safety pin 116 in its function of locking actuation. The thinned region 144 provides a distal extension of the safety pin 116 to allow this function to be achieved. If the safety pin 116 was instead formed so as to be enlarged along its whole axial extent, an inconvenient, for the user, amount of axial movement (and thus turning) of the safety cap 102 would be required to place the safety cap 102 in the safety released position.

Figure 18A:
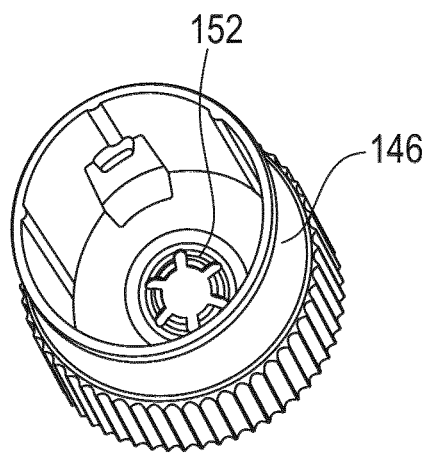
FIGS. 18(a), and 18(b), and 18(c) how an alternate construction in which the pin is separately formed and mechanically attached to a body of the safety cap, rather than the body of the safety cap and safety pin being formed as an integrally molded piece as shown in FIGS. 16 and 17, FIGS. 19(a), 19(b) and 19(c) show steps of operation of the safety cap and the injector in longitudinal cross-section. The safety cap is moved from an actuation locked position (FIG. 19(a)) in which the holding arms of the injector are blocked from inward deflection by the safety pin, thereby locking the injector against actuation. The safety cap moves to a safety released position (FIG. 19(b)) in which the safety pin is moved out of a blocking arrangement with the holding arms so that the injector is ready for actuation.
Figure 18B:
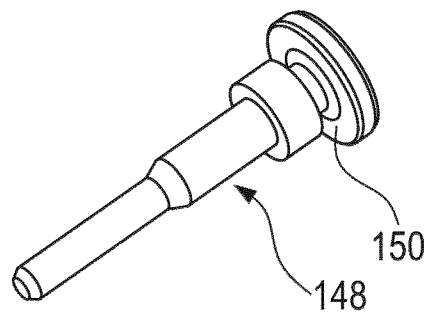
Figure 18C:
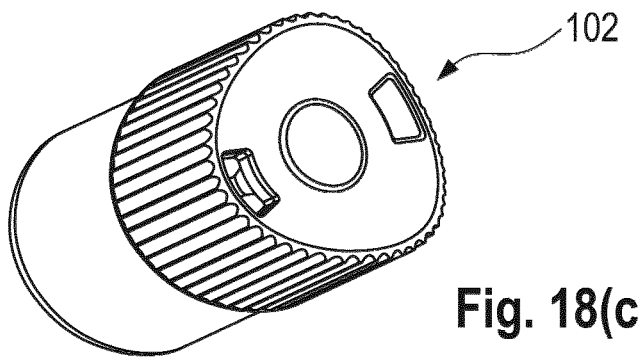

Referring to FIG. 18, a two piece assembly for the safety cap 102 is shown. The safety cap 102 comprises body piece 146 forming the sleeve body 114 of the safety cap 102 and a safety pin piece 148. The safety pin piece 148 comprises a groove 150 that engages teeth 150 of the body piece 146 in a resilient snap fit. When assembled, the safety cap 102 presents a closed rear surface or rear cover portion to a user at an area longitudinally aligned with the safety pin 116. The closed area is at least as large as a largest cross-sectional area of the safety pin 116. The two pieces 146, 148 are separately injection moulded, whereas in the embodiment of FIG. 16 the safety pin 116 is integrally injection moulded with the rest of the safety caps 102.

Figure 19A:
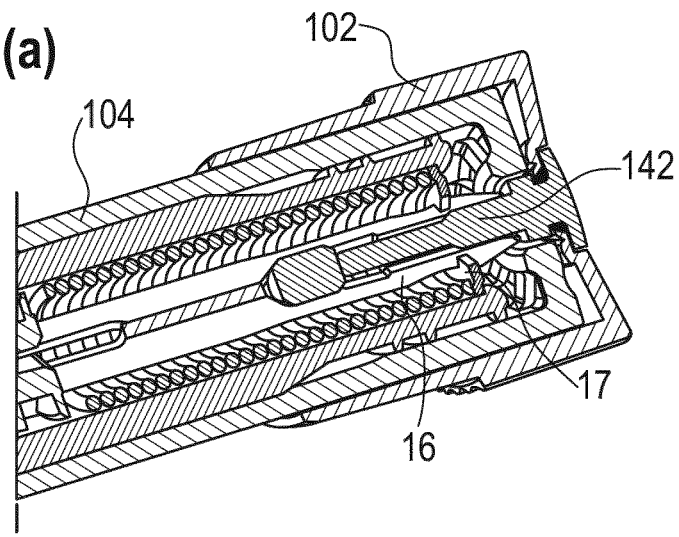
In FIG. 19(c), the holding arms have been deflected inward by movement of the trigger sleeve to actuate the injection operation.

Referring to FIG. 19, an operating sequence for the injector 100 can be seen. In FIG. 19(a), the safety cap 102 is in a relatively distal position along the outer housing 104 corresponding to the actuation locked position of the safety pin 116. Although the two piece safety cap 102 is shown, the following operation is equally applicable to the one piece construction. The safety cap 102 is held in the relatively distal position by the stop surface 138 being positioned behind the first ridge 128 such that the protrusion 136 is held in a start position of the first helical groove 124. The safety cap 102 is rotatable about a longitudinal axis of the injector 100, whereby the protrusion 136 rides in the first helical groove 124, but first the user must apply an extra turning force to overcome a force bump provided by the requirement to push the stop surface 138 over the first ridge 128. Thus, the force bump defined by the first ridge 128 ensures that the safety cap 102 is not rotated and the safety pin 116 is not moved from the actuation locked state unintentionally.

In the actuation locked position of FIG. 19(a), the holding arms 16 (and particularly teeth thereof) are retained on the holding disc 17 and cannot be disengaged from the disc 17 because the enlarged region 142 of the safety pin 116 is blocking inward deflection of the holding arms 16. The injector 100 is thus locked against actuation.

Figure 19B:
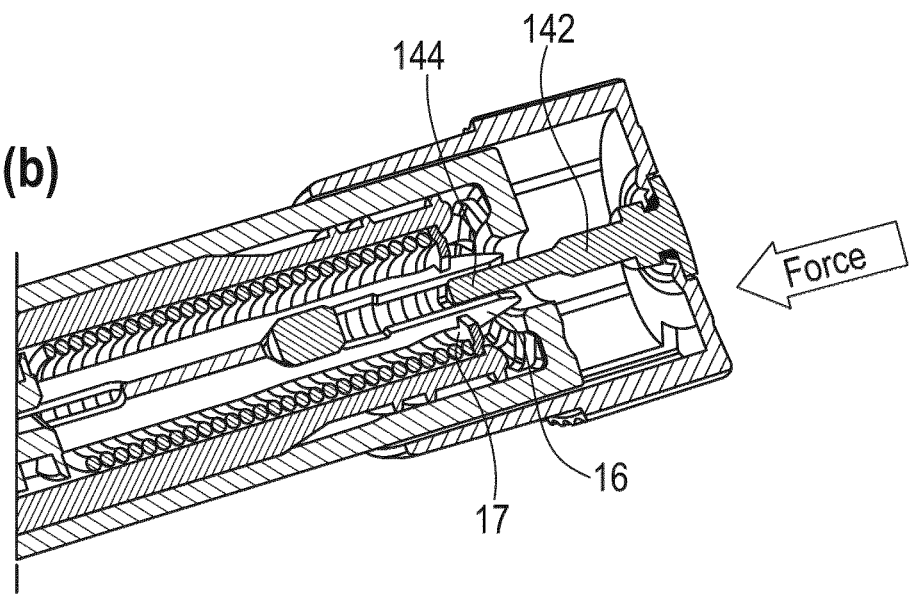

In FIG. 19(b), the safety cap 102 has been rotated to the end of the first helical groove 124 and is held at the end by the stop surface 138 having moved beyond the second ridge 130. The force bump in moving the stop surface over the second ridge 130 provides a tactile indication to the user of the safety released position of the safety pin 116 having been reached. The safety cap 102 may, if the user wishes, be turned in the opposite direction to return the safety cap 102 to the relatively distal position corresponding to the actuation locked position shown in FIG. 19(a). To do so, the stop surface 138 must be moved back over the second ridge 130 and the associated force bump.

In the configuration of FIG. 19(b), the safety pin 116 is in the safety released position. That is, the enlarged region 142 of the safety pin 116 is no longer disposed between the holding arm 16 such that the holding arms 16 are free to be released from the holding disc 17. Thus, the injector 100 is in a safety released state and the safety pin 116 is in a safety released position in which the injector 100 is ready and free to be actuated. The thinned portion 144 of the safety pin 116 remains disposed between the holding arms 16, but does not prevent sufficient inward deflection thereof to release a retention surface of the holding disc 17.

Figure 19C:
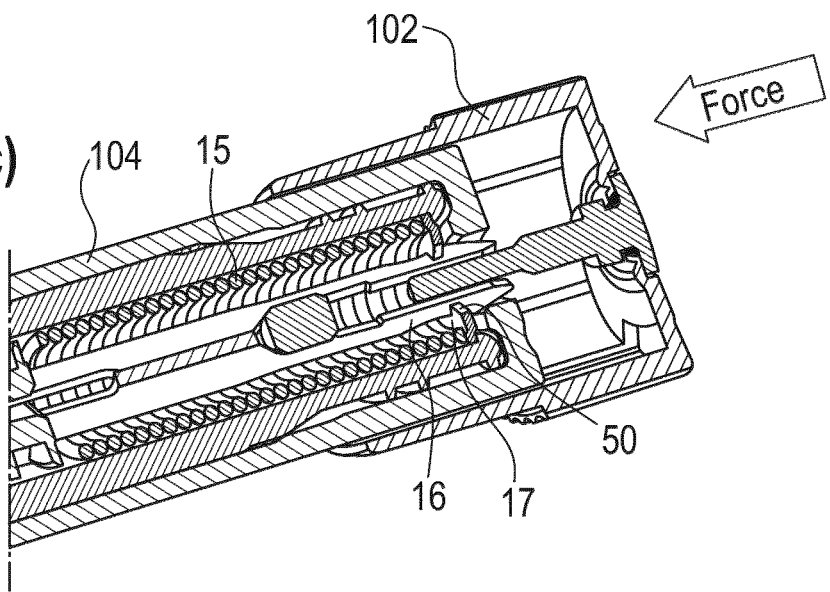

In FIG. 19(c), the user has applied forward or distally directed force either to the outer housing 104 or the safety cap 102 as shown by the respective force arrows. This force causes movement of the outer housing 104 relative to the holding arms 16 to move an activation surface 50 into engagement with a proximal end (forming arrowheads) of the holding arms 16 so as to deflect the holding arms 16 inwardly. The holding arms 16 are thus released from the holding disc 17 to release the drive spring 15. The drive spring 15 expands to release energy for driving the injection operation as has been explained above.

In FIGS. 20 to 34, a second embodiment of a safety pin 216, incorporated in a safety cap 202, is shown. The safety cap 202 is applied to a rear end portion of the housing 9 of the injector 1 of FIGS. 1 to 10. However, the present safety cap 202 could be applied to other autoinjectors, such as the prior art autoinjectors identified in the background section above, which make use of a safety pin to lock an actuation mechanism.

Figure 20:
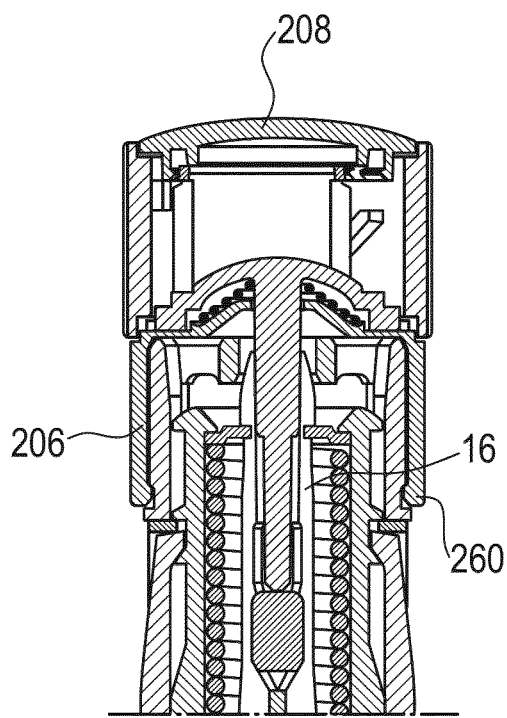
FIGS. 20 and 21 show a second embodiment of a safety cap according to the present invention. The safety cap is mounted to a rear end portion of the injector of FIGS. 1 to 10. A longitudinal cross-section is provided to show internal components whereby a safety pin is moved from an actuation locked position in FIG. 20 to a safety released position in FIG. 21 without rotation of the safety pin and without axial movement of the safety cap.
Figure 21:
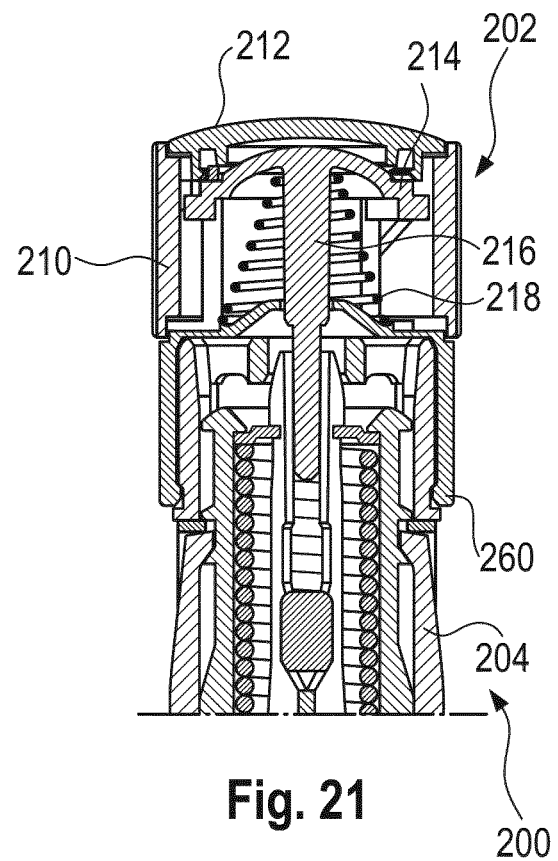
Figure 22:
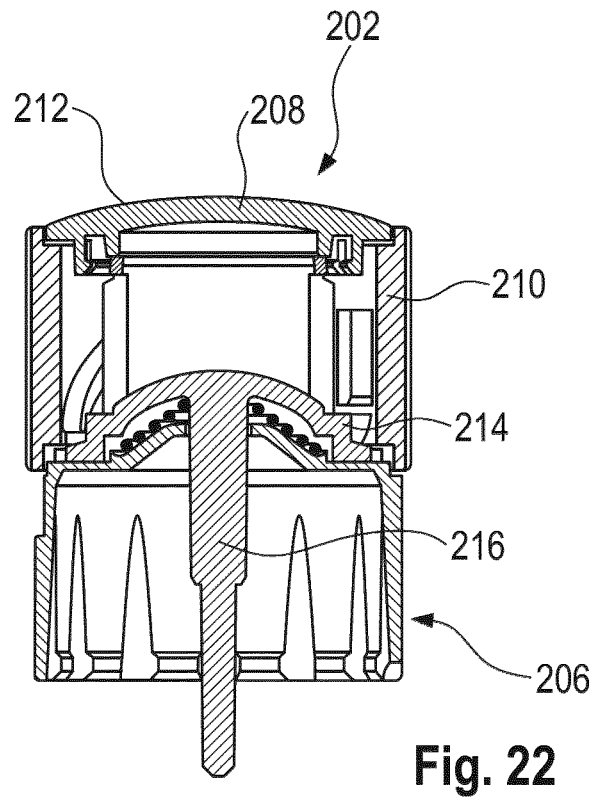
FIG. 22 shows a longitudinal cross-section of the safety cap on its own. The safety cap comprises a base, a safety pin, a rotatable part for moving the safety cap, a base for mounting the safety cap to an injector and a cover to provide a closed rear face for the injector.

In FIGS. 20 to 22, the component parts of the safety cap 202 can be seen in cross-section. The safety cap 202 comprises a base 206 as shown also in FIG. 29, which mounts to a rear end portion of an injector 200. The base 206 comprises a sleeve portion 220 that receives the rear end portion of the housing 204 of the injector 200 therein. The base 206 comprises upstanding flanges 224 extending from the sleeve portion 222. The upstanding flanges 224 define an axially extending space between them, which space receives radial extensions 230 therebetween of an axially moveable part 212 (further shown in FIG. 27) to guide axial translation of the axially translatable part 212. That is, the flanges 224 are opposed and define a pair of diametrically opposed axially extending spaces therebetween. The spaces respectively receive one of the radial extensions 230 of the axially movable part 212 (or axially translatable part) such that the flanges 224 guide axial movement of the flanges 224 to prevent rotation of the axially movable part 212. The upstanding flanges 224 of the base 212 are further configured to mount a cover 208 at the top (or rear end) thereof. The base 206 comprises an indicator panel 222 along which a flag 240 of a rotatable part 210 (see also FIG. 26) moves to provide a visual indication of whether the safety pin 216 is in the actuation locked position of FIG. 20 or the safety released position of FIG. 21. The indicator panel may have different colours, icons representing locked and unlocked, or other visually differentiable indicia representing the position of the safety pin 216.

The safety cap 202 further comprises a rotatable part 210 (see also FIG. 26) mounted about the upstanding flanges 224 and atop a rim 226 of the base 206 for rotation (pure rotation, not including axial movement) about a longitudinal axis of the injector. The rotatable part 210 comprises an internal helical thread 242 that is received in a diagonal (relative to the longitudinal axis) groove 232 in a radial face of each radial extension 230. Cooperation between one of the grooves 232 and the internal helical thread 242 causes translation of the axially translatable part 212 and the associated safety pin 216 upon rotation of the rotatable part to move the safety pin 216 from an actuation locked position as shown in FIG. 20 to a safety released position as shown in FIG. 21. The safety pin mover of the present disclosure thus comprises the grooves 232, the thread 242, the axially translatable part 212 and the rotatable part 210 of the present embodiment. The thread 242 can also be described as a guide and is in the form of a helical rib. The thread 242 cooperates with the grooves 232 to transmit rotation of the rotatable part 210 to translation of the safety pin 216. The rotatable part 210 comprises the indicator flag 240, which protrudes relative to a front end edge thereof. The rotatable part 210 comprises axially extending ribs distributed about the full circumference of the rotatable part 210 in order to increase grip for turning by a user. The rotatable part 210 is in the form of a band open at both front and rear ends.

The safety cap 202 comprises the axially translatable part 212. The axially translatable part 212 includes a cap portion 238 to which the safety pin 216 depends. The safety pin 216 is axially centrally located and extends axially. The safety pin 216 has a rear enlarged region and forward thinned region for the purposes explained above with respect to FIGS. 11 to 19. The cap portion 238 is solid disc formed and has diametrically opposed radial extensions 230. The radial extensions 230 include the diagonal groove 232 and a stop recess 236 in the groove 232. The radial extensions 230 are guided in axial translation by sliding movement in the space between the flanges 224 of the base 206. The stop recess 236 receives a bump 244 on the helical thread 242 of the rotatable part 210 to define a stop position at the start of the helical thread 242 so that there is a force bump to overcome in order to turn the rotatable part 202 to begin moving the axially translatable part 212 and the safety pin 216 out of the actuation locked position of FIG. 20. The force bump prevents unintended movement out of the actuation locked position. The axially translatable part 212 is mounted for axial translation within a space defined axially between the cover 208 (rear cover portion) and a platform 228 of the base 206 from which the upstanding flanges 224 extend rearwardly, and defined radially within the rotatable part 210.

The safety cap 202 further comprises a spring 218 that biases the axially translatable part 212 from the actuation locked position of the safety pin 216 in which the axially translatable part 212 is forwardly or distally disposed and the safety released position of the safety pin 216 in which the axially translatable part 212 is proximally or rearwardly disposed. The spring 218 is conically formed and a thin end of the cone (truncated cone) engages an underside of the cap portion 238 of the safety cap 212 and a base end of the cone engages the platform 228 of the base 216. The spring 218 is disposed radially within the upstanding flanges 224 of the base 206. The spring 218 functions to automatically complete axial movement of the axially translatable part 212 from the actuation locked position of the safety pin 216 to the safety released position once the force bump defined by the stop recess 236 and the bump 244 has been overcome by a user turning the rotatable part 210.

The safety cap 202 comprises the cover 208, which is dome (convex) shaped and serves as a rear end face of the safety cap 202 and also the injector 200. The cover 208 defines a closed rear end face that does not have a through opening at a central area axially coinciding with the safety pin 216, where the central area is at least as large as a maximum cross-section of the safety pin 216. The cover 208 comprises teeth 250 depending from an underside of the cover 208 that are annularly distributed. Further, a continuous annular ridge 252 also depends from an underside of the cover 208 and is disposed radially inside the annulus of teeth 250 to define an annular space therebetween. The teeth 250 function to snap fit engage a groove 229 on the upstanding flanges 224 of the base 206 to mount the base 206 and the cover 208 together. A rearward edge of the upstanding flanges is received in the annular space between the teeth 250 and the ridge 252 of the cover 208 to secure the cover 208 and the flanges 224 in place. A peripheral portion 254 of the cover 208 extending radially outward of the teeth 250 positions on a step 244 formed inside the rotatable part 210, thereby axially securing the rotatable part 210 relative to the cover 208 and thus the base 206.

Figure 23:
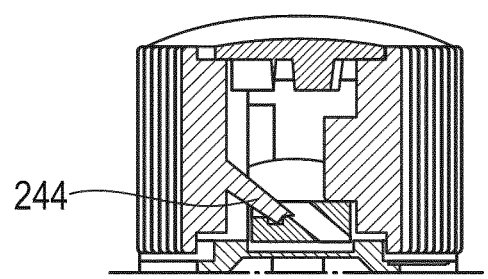
FIGS. 23 to 25 show how an internal thread of the rotatable part and a groove of the safety cap cooperate to translate the safety pin axially upon rotation of the rotatable part.

Referring to FIGS. 20, 21 and 23 to 25, a sequence of operation of the safety cap 202 is shown. In the configuration of FIG. 23, the bump 244 of the helical thread 242 of the rotatable part 210 is engaged in the stop recess 236 of the diagonal groove 232 of the axially translatable part 212. Engagement of the bump 244 and the stop recess 236 holds the spring 218 in a contracted form. In this state, the pin 216 is disposed between the holding arms 16 to prevent deflection inwards by blocking such that actuation of the injector 200 is prevented. The condition of FIGS. 20 and 23 is thus an actuation locked condition of the injector 200 corresponding to an actuation locked position of the safety pin 216. In this state, the flag 240 of the rotatable part 210 aligns with a visual indictor of actuation locked on the indication panel 222 of the base 206.

Figure 24:
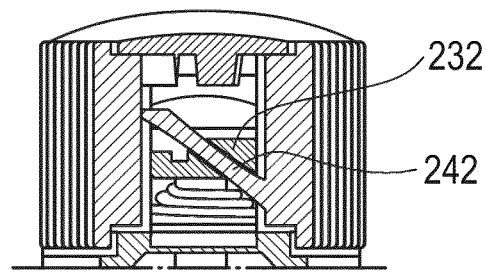
Figure 25:
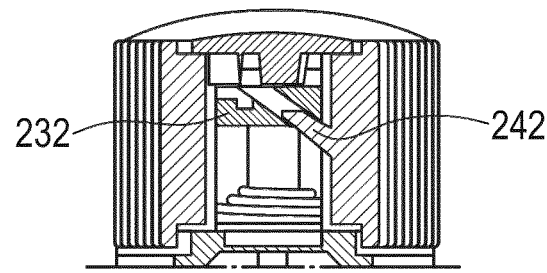
Figure 26:
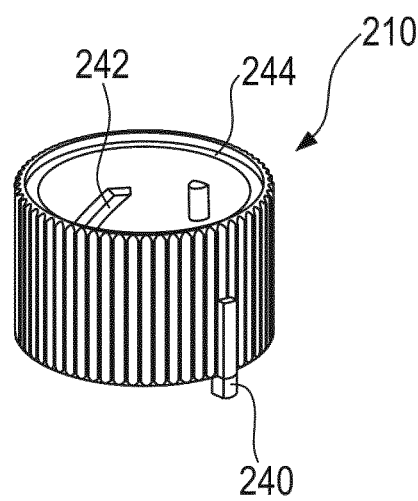
FIGS. 26 to 29 show various pieces of the safety cap including the rotatable part (FIG. 26), the safety cap (FIG. 27), the cover (FIG. 28) and the base (FIG. 29).
Figure 27:
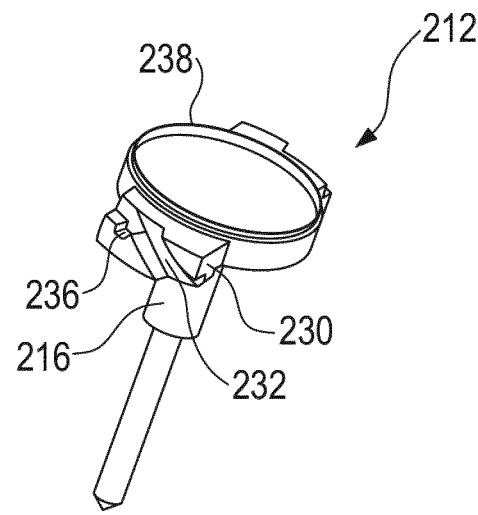
Figure 28:
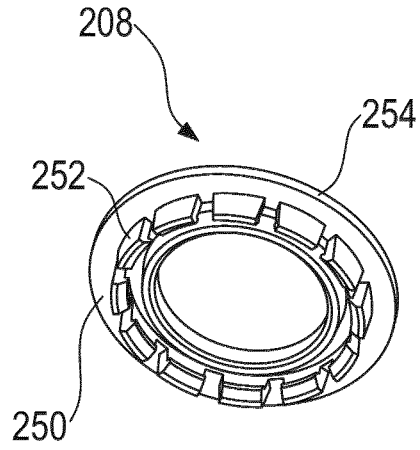

When an injection operation is required, a user applies a turning moment to the rotatable part 210 by gripping the longitudinally extending ribs, thereby releasing the bump 244 from the stop recess 236. The spring 218 is thus able to expand to move the groove 232 of the axially translatable part 212 along the helical thread 242, thereby translating the axially translatable part 212 axially, guided by the space between the flanges 224 of the base 206, and rotating the rotatable part 210 about the longitudinal axis. Alternatively, the user may complete the rotation of the rotatable part 210 about the longitudinal axis and the spring 218 may merely facilitate movement of the axially translatable part 212 and the rotatable part 210. The axially translatable part 212 translates axially until the extensions 230 thereof engages stop protrusions 227 of the base 220 extending into the space between the flanges 224 to define an end stop position of axial translation of the axially translatable part 212. This end stop position may be configured to provide a tactile indication to the user that the safety released position of the safety pin has been reached, e.g. through the spring 218 may cause the extensions 230 to strike the stop protrusions 227 or at least one stop protrusion so as to provide a tactile indication. The axially translatable part 212 is, in this way, located with the grooves 232 thereof at the end of the helical thread 242 of the rotatable part 210. FIG. 24 shows the diagonal groove 232 part way along the helical thread 242. In FIG. 25, the axially translatable part 212 has reached the end stop position, whereby the diagonal groove 232 is located at the end of the helical thread 242. Here, the safety pin 216 is retracted rearwardly out of blocking relation with the holding arms 16 to free the holding arms 16 for inward deflection to actuate the injection operation. Referring to FIG. 30, and comparing it to FIG. 32, the indicator flag 240 of the rotatable part 210 has moved along the indicator panel 222 of the base 206 to a position aligned with a visual indicator (not shown) of the safety pin 216 being in a safety released position. The injector 200 is now free to be actuated in the manner described above with respect to the embodiment of FIGS. 11 to 19, namely by shifting the outer housing 204 axially relative to the holding arms 16, whether by the user applying force directly to the outer housing 204 or to the safety cap 202.

Figure 29:
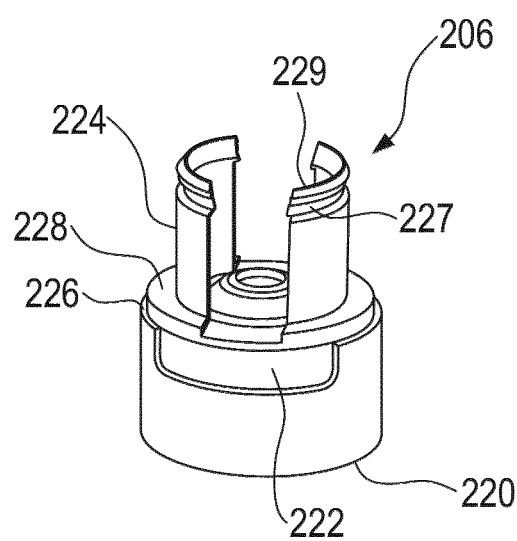

A method of assembly of the safety cap 202 can be understood from FIGS. 27 to 34. Referring to FIGS. 29 and 30, the rotatable part 210 is placed on the base 206 so as to bare during rotation on the platform 228 and the rim 226, with the step 244 of the rotatable part 210 being disposed in baring contact with the platform 228 of the base 206. The spring 218 is located within the flanges 224 of the base 206.

The rotatable part 210 is rotated to the safety released position shown in FIG. 30 to align the internal thread 242 with the space between the flanges 224. The axially translatable part 212 can now be positioned with the radial extensions 230 aligned with the space between the flanges 224 and moved along the space. The radial extensions 230 will have to be forced over the stop protrusion 227 of the flanges 224 by resilient deflection of the flanges 224 away from each other. The groove 232 of one of the radial extensions 230 (the extensions 230 are symmetrical so it matters not which one receives the groove 232) receives the end of the helical thread 242 of the rotatable part 210. The axially translatable part 212 can be pushed axially from the position shown in FIG. 31 to the position shown in FIG. 32, so that the groove 232 slides along the thread 242 to the start of the thread (causing rotation of the rotatable part 210) until the bump 244 of the thread 242 engages in the stop recess 236 of the axially translatable part 212. The axially translatable part 212 is thus held in the actuation locked position of the associated safety pin 216.

In order to axially hold the base 206 and the rotatable part in axially fixed relation, the cover 208 is mounted to the upstanding flanges 224 by snap fit engagement of the teeth 250 of the cover 208 to the annular groove 229 of the upstanding flanges 224 of the base 206. The periphery 254 of the cover 208 is seated in the step 244 of the rotatable part 210. In this way, a modular safety cap 202 is provided for mounting to a rear end of a housing of an injector, such as the injector of FIGS. 1 to 10 or other known autoinjector requiring a safety pin to be moved rearward from an actuation locked position to an actuation ready position.

Referring to FIGS. 20, 33 and 34, the modular safety cap 202 is mounted to the injector 200 by forward teeth 260 of the base 206 resiliently engaging in an annular groove 250 of the outer housing 204 of the injector 200 to axially fix the safety cap 202 and the injector 200 together. Thus, the teeth 260 and the groove 250 form holding surfaces for preventing the safety cap from being removed from the housing of the injector when the safety pin 216 is in the safety released position. In this way, the hole 72 (FIG. 5) into which the pin 216 extends is covered by the safety cap (specifically the rear cover portion 208 irrespective of the safety pin position. The forward teeth 260 of the base 206 are located on a forward end of the sleeve body 220 of the base 206 and protrude radially inwardly. The sleeve body 220 also comprises an axially extending rib 262 on the inside thereof to engage an axially extending positioning groove 252 in the outer housing 204 of the injector to circumferentially fix the base 206 and the outer housing 204 of the injector 200.

Various modifications could be made to the safety caps disclosed herein with respect to FIGS. 11 to 34 and still be encompassed by the present invention. For example, safety pin mover comprising an axially movable part that is grasped by a user can be envisaged, rather than the rotatable user grasping part embodiments disclosed herein. In such an alternative embodiment, the user graspable part of the safety pin mover is movable axially along the outer housing, perhaps along a guiding groove or other guide structure between start and end stop positions, to move the safety pin between actuation locked and safety released positions.

In another variation, a spring could be included in the embodiment of FIGS. 11 to 19 to bias the safety cap to the relatively proximal position of FIG. 12 to assist/automatically complete movement of the safety pin to the safety released position, thereby replicating the function of the spring 218 of the embodiment of FIGS. 20 to 34.

Figure 14:
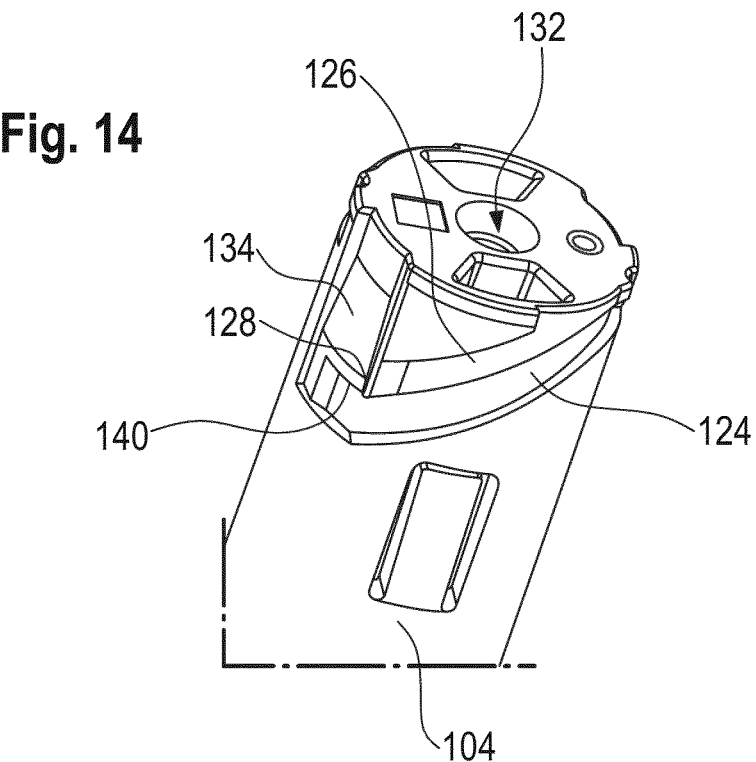
FIGS. 14 and 15 show an external view of a rear end of the injector with the safety cap not in place. A thread is formed in an outer housing of the injector (to which the safety cap is to be mounted).
Figure 15:
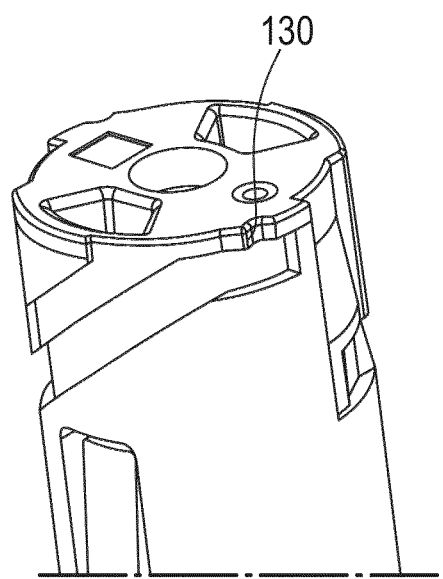

Referring to FIGS. 14 and 16, the groove 124 could itself include start and end stop ridges that interact with the protrusion 136 to provide the force bump, thereby eliminating the need for the second groove 126 and associated stop surfaces 128, 130 and 138.

In a further potential modification, and with reference to FIGS. 23 to 25, the thread 242 of the rotatable part 210 could include a second bump that engages with the recess 236 of the groove 232 of the axially translatable part or another such recess 236 to provide a means for tactile indicating the end stop position. It can be envisaged, particularly with respect to the above modification including the second means for tactile indication in the second embodiment, that the spring is not included in the second embodiment such that movement of the rotatable part 210 is effected only by manual force, i.e. the movement is not spring assisted.

Another variation, constituting a third embodiment of the safety pin and injector, is disclosed with respect to FIGS. 35 to 38, whereby a safety pin is non-removably configurable between the safety released and actuation locked positions. In the foregoing embodiments, the safety pin has been axially movable, specifically proximally movable, between the safety released and actuation locked positions. In the present embodiment, the safety pin rotates between the safety released and actuation locked positions. The safety pin and safety cap shown in FIGS. 35 to 38 are adapted for use with an injector 1 as disclosed with respect to FIGS. 1 to 10. In FIGS. 35 to 38, reference signs have been followed by a prime (') as compared to corresponding features in FIGS. 1 to 10. The same reference signs have been used, merely followed by a prime, to indicate substantial equivalency of features. In addition to reference some features of the injector 1' shown in FIGS. 35 to 38, the following discussion also references the injector 1 of FIGS. 1 to 10.

Figure 35:
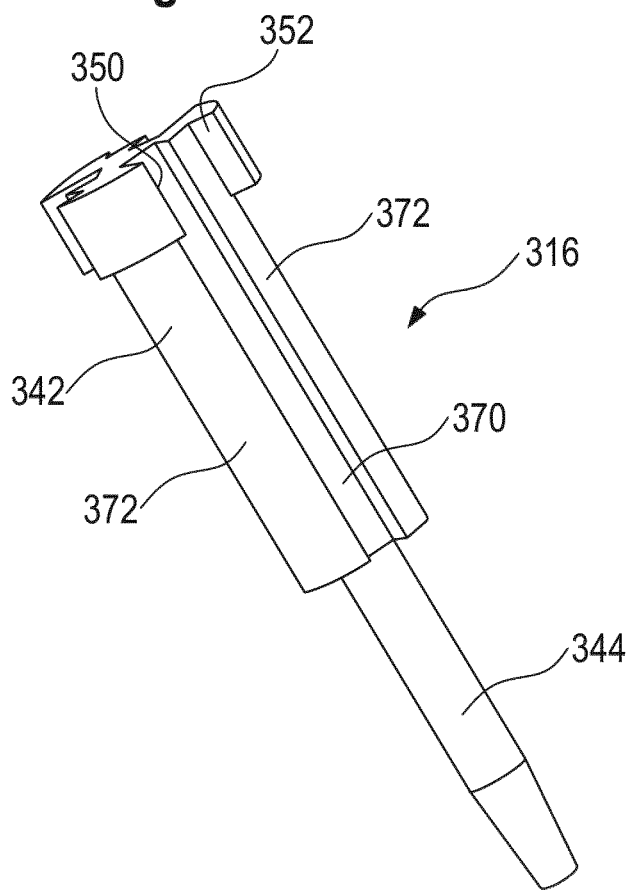
FIG. 35 shows an alternative embodiment of a safety pin, which is rotatable between actuation locked and safety released positions.

Referring to FIG. 35, the safety pin 316 includes one or more blocking surfaces 372 and one or more grooves or cut-outs 370 that are radially recessed relative to the one or more blocking surfaces 372. The safety pin 316 includes alternating blocking surfaces 372 and cut-outs 370 in the circumferential direction. In the exemplary embodiment, there are three pairs of cut-outs 370 and blocking surfaces 372 distributed circumferentially about the safety pin 316. With additional reference to the description of the injector 1 provided above with respect to FIGS. 1 to 10, each cut-out 370 is sufficiently recessed to receive therein a holding arm 16' (see also FIGS. 37 and 38) of the actuator to allow the holding arm 16' to be radially deflected to disengage the holding disc 17' to release the spring 15' to actuate the injection device 1', thereby placing the injector 1' in an actuation ready state. The blocking surfaces 372 of the safety pin, by contrast, serve to lock the holding arms 16' in the radial direction with respect to the longitudinal axis 13 and prevents release of the holding arms 16' from the holding surface of the holding disc 17', thereby placing the injection device 1' in the actuation locked state. The safety pin 316 is rotatable about the longitudinal axis 13 to align either the cut-outs 370 or the blocking surfaces 372 with the holding arms 16' to place the safety pin either in safety released or actuation locked positions.

The safety pin 316 is elongate and is configured for extending along the central longitudinal axis 13 of the injector 1'. The safety pin 316 has a radially enlarged, axially extending region 342 and a radially thinned, axially extending region 344. The radially enlarged region 342 is rearwardly disposed to the radially thinned region 344. The radially enlarged region 342 includes the blocking surfaces 372 for engaging the holding arms 16' to lock them onto the holding disc 17'. The radially enlarged region 342 also includes the cut-outs 370 that are recessed for receiving inward deflection of the holding arms 16' to actuate the injector 1'. The thinned region 344 serves at least a manufacturing function as described above with respect to FIGS. 10 and 16.

Figure 36:
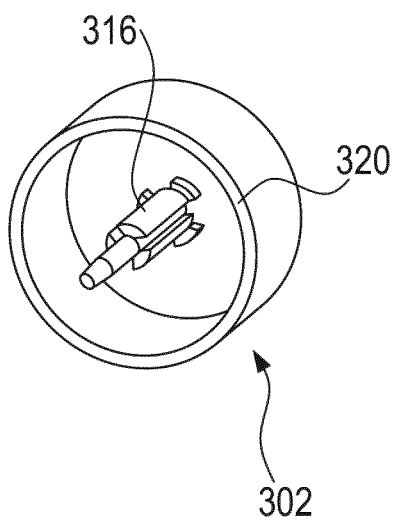
FIG. 36 shows the safety pin of FIG. 35 included in a safety cap.

Referring now to FIG. 36, the safety pin 316 is incorporated, in the present embodiment, in a safety cap 302 (which itself forms both a rotatable part and safety pin mover as described herein). The safety pin 316 may be integral with the safety cap 302 or a separate piece attached thereto. The safety cap 302 and the safety pin 316 are rotationally fixed so that they rotate in conjunction. The safety cap 302 includes a closed or solid rear surface 306 (FIG. 38), a sleeve 320 and the safety pin 316 extending distally and normally relative to the rear surface 306. The safety pin 316 and the sleeve 320 are coaxially arranged in the shown embodiment. The safety pin 316 and the sleeve 320 define a loop shaped space therebetween into which the rear end portion of the housing 9 of the injector 1' is able to be inserted to mount the safety cap 302 to the injector 1'. The safety cap 302 is to be mounted with the sleeve 320 extending over a rear end portion of the housing 9 and with the safety pin 316 extending through the opening 72 in the holding disc 17' (as described with reference to FIGS. 1 to 10 above) and through a corresponding opening in the housing 9.

The safety cap 302 is rotatable between first and second stop positions corresponding respectively to the safety pin 316 being in the actuation locked position and the safety pin being in the safety released position. The first and second stop positions are provided, in the present embodiment, by stop surfaces 350, 352 provided as part of the safety pin 316. The stop surfaces 350, 352 engage respective holding arms 16' and only allow a limited degree of rotation of the safety cap 302. When first stop surfaces 350, facing in a first rotational direction, engage holding arms 16', the cut-outs 370 are radially aligned with the holding arms 16' to allow actuation of the injector 1'. When second stop surfaces 352, facing in a second rotational direction, engage the holding arms 16', the blocking surfaces 372 are radially aligned with the holding arms 16' to prevent actuation of the injector 1'. It can be envisaged that corresponding stop surfaces could instead be located elsewhere such as on the inside of the sleeve 320 and the outside of the housing 9. The injector 1' may comprise at least one of first and second detent arrangements (not shown) for holding at least one of the stop positions and requiring a force bump to release the at least one of first and second detent arrangements, such as detent arrangements provided between the sleeve 320 and the housing 9. The injector 1' may comprise a spring (not shown) for biasing the safety cap 302 to the safety released position such that once rotation of the safety cap 302 has been initiated (e.g. a force bump has been overcome), the spring is able to auto complete the rotation of the safety cap 302 from the actuation locked state of the injector 1' to the safety released state of the injector 1'.

The safety cap 302 may be resiliently, snap-fit mounted to the outer housing 9 of the injector 1' via the sleeve 320. The sleeve 320 and the housing 9 may include one or more cooperating projections and recesses to mount the sleeve and the housing 9 together. For example, the housing 9 may include a circumferential groove similar to that shown in FIG. 33 for receiving one or more projections of the sleeve 320. In this way, interfacing holding surfaces are provided between the housing 9 and the safety cap 302 for preventing movement of the safety cap 302 in the rearward direction when the safety pin 316 is in the safety released position.

Figure 37:
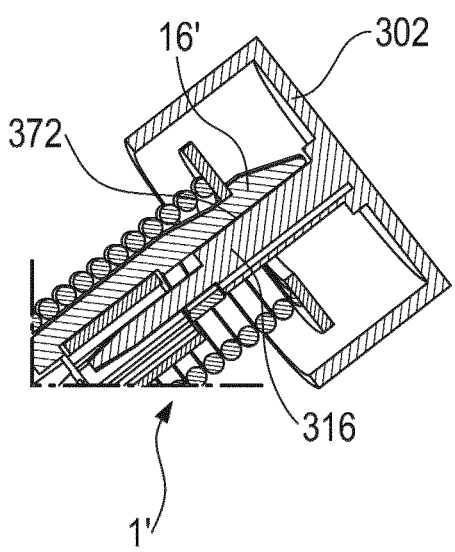
FIGS. 37 and 38 show the safety cap in relatively rotated positions corresponding to the actuation locked and safety released positions of the safety pin of FIG. 35.

Referring to FIG. 37, the safety cap 302 is shown mounted to a schematically drawn injector 1', which is largely the same as the injector 1 of FIGS. 1 to 10. The injector 1' includes a housing 9 (according to that shown in FIGS. 1 to 10), a spring 15' as described for the spring 15 previously, holding arms 16' functionally as described previously with respect to holding arms 16 and a holding disc 17' substantially as described previously for the holding disc 17. However, the injector 1' includes three holding arms 16', rather than the four holding arms 16 of the embodiment of FIGS. 1 to 10. Otherwise, the previously described features of the injector 1 are applicable to the injector 1'. It can be envisaged that fewer holding arms 16' could be utilised to allow for a greater degree of rotation of the safety pin 316 between the actuation locked and safety released positions. For example, there could be one or two holding arms 16'. The number of holding arms 16' is related to the amount of rotation between the actuation locked and released positions. For example, one holding arm 16' would allow for 180° rotation, two holding arms allows for 90° rotation, three holding arms allows for 60° rotation, etc. It can also be envisaged that other mechanisms for releasing the actuator, e.g. releasing the spring 15' of the actuator, for actuating automated injection could be provided.

The safety cap 302 of FIG. 37 has the safety pin 316 in the actuation locked position. In this position, the blocking surfaces 372 of the safety pin 316 are aligned with the holding arms 16' to prevent inward deflection thereof and thus to lock the injector 1' against actuation. In this position, the first stop surfaces 350 rest against respective holding arms 16' so that the safety cap 302 is only able to rotated in the direction of safety release.

Figure 38:
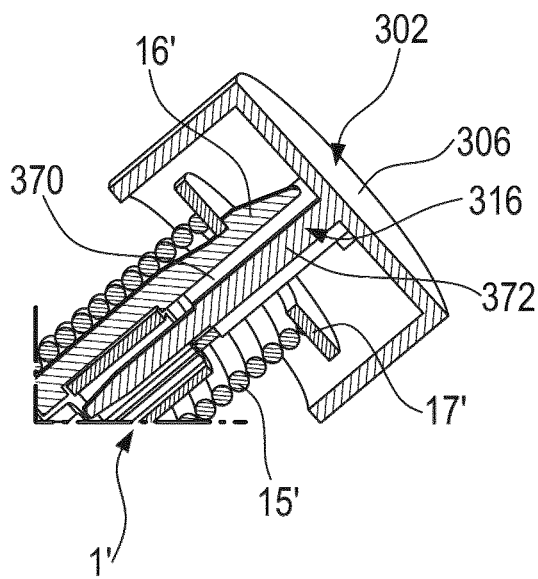

In FIG. 38, an operator has manually grasped and rotated the externally positioned safety cap 302 and rotated the safety cap 302 until the second stop surfaces 352 are engaged against the holding arms 16'. In the configuration of FIG. 38, the safety cap 302 remains coupled to the injector 1' so that there can be no confusion as to which end of the injector 1' is the needle end. In this position, the cut-outs 372 are aligned with the holding arms 16' and the blocking surfaces 372 have been rotated out of alignment therewith. The cut-outs provide sufficient recess space to allow the holding arms 16' to be deflected radially inwardly upon pushing an end surface of the needle protection element 7 against a user's skin, to thereby release the holding arms 16' from the holding disc 17 to actuate the injector 1'.

The safety cap 302 may be a one way only device, but is preferably (as with the other embodiments described herein) reversible so that a transition from actuation locked to safety released is possible and a transition back to actuation locked is possible.

Various modifications to the embodiment of FIGS. 35 to 38 could be made. For example, ribs or other grip enhancement features could be included on the outside of the safety cap 302. Further, an indicator could be provided for visually indicating when the safety pin 316 is in the safety released position and for indicating when the safety pin 316 is in the actuation locked position in a visually differentiable manner. One exemplary indicator could be a flag on the safety cap 302 and different markers (icons, graphics, alphanumeric characters, colours, etc.) could be included on the housing 9 (or the flag could be on the housing and the markers on the safety cap), similar to that described with respect to the embodiment of FIGS. 20 to 34. The flag is rotatable in conjunction with the safety cap 302 to align with visually different markers (such as the icons, graphics, alphanumeric characters, colours, etc.) in the safety released and actuation locked positions. Alternatively, the safety cap 302 could include one or more windows that align with different markers (colours, graphics, alphanumeric characters, icons, etc.) depending upon the rotational position of the safety cap 302.

While exemplary embodiments have been presented in the foregoing detailed description, it should be appreciated that a vast number of variations exist. It should also be appreciated that the exemplary embodiments are only examples, and are not intended to limit the scope, applicability, or configuration of the disclosure in any way. Rather, the foregoing detailed description will provide those skilled in the art with a convenient road map for implementing the exemplary embodiments. It should be understood that various changes can be made in the function and arrangement of elements without departing from the scope of the disclosure as set forth in the appended claims and the legal equivalents thereof.

Items of the Disclosure

The Following Numbered Items Relate to the First, Second and Third Embodiments, Unless Stated Otherwise.

1. An injector for performing an injection operation comprising a housing, a needle extendable from a front end of the housing, a rear end of the housing and a longitudinal axis extending between the front end and the rear end, a safety pin in an actuation locked position coupled to the housing and moveable to a safety released position coupled to the housing, wherein the injector is locked against actuation when the safety pin is in the actuation locked position and the injector is ready for actuation of the injection operation when the safety pin is in the safety released position.

2. The injector of any preceding item, wherein the safety pin extends through an opening in a rear end face of the housing, and the needle of the injector is extendable through a front end face of the housing.

3. The injector of item 2, wherein the opening is covered by a safety cap comprising the safety pin when the safety pin is in the safety released position.

4. The injector of item 2 or 3, wherein the safety pin remains disposed in the opening in the safety released position.

5. The injector of any one of the preceding items, wherein the safety pin is elongate and extends along the longitudinal axis of the injector.

6. The injector of item 5, wherein the safety pin extends along a central longitudinal axis of the injector.

7. The injector of any one of the preceding items, wherein the safety pin is moveable along the longitudinal axis from the actuation locked position to the safety released position.

8. The injector of any preceding item, wherein the injector comprises a safety cap comprising the safety pin.

9. The injector of item 8, wherein the safety cap covers a rear end face of the housing.

10. The injector of item 8 or 9, wherein the safety cap has a closed rear surface in an area longitudinally aligned with a rear end of the safety pin.

11. The injector of item 8, 9 or 10, wherein the safety cap comprises a sleeve extending over a rear end portion of the housing of the injector.

12. The injector of item 11, wherein the safety cap is mounted to the outer surface of the housing via the sleeve.

13. The injector of any one of items 8 to 12, wherein the safety cap comprises a rear cover portion and the safety pin is disposed on a front side of the rear cover portion, preferably centrally with respect to the rear cover portion.

14. The injector of any one of the preceding items, comprising a guide and structure cooperating with the guide to guide movement of the safety pin between the actuation locked position and the safety released position. This item relates particularly to the first and second embodiments.

15. The injector of item 14, wherein the guide extends from a first position corresponding to the actuation locked position and a second position corresponding to the safety released position. This item relates particularly to the first and second embodiments.

16. The injector of item 14 or 15, wherein the guide and structure cooperating with the guide comprises a groove and a cooperating projection for riding therein or a thread and a cooperating groove. This item relates particularly to the first and second embodiments.

17. The injector of item 16, wherein the groove or the thread extend helically or diagonally relative to the longitudinal axis. This item relates particularly to the first and second embodiments.

18. The injector of item 16 or 17, wherein the groove and the cooperating projection are disposed between an outer surface of the housing and the inner surface of the sleeve of the safety cap. This item relates particularly to the first embodiment.

19. The injector of item 18, wherein the groove is defined in the outer surface of the housing and the projection is defined on an inner surface of the sleeve of the safety cap. This item relates particularly to the first embodiment.

20. The injector of item 16, wherein the safety cap comprises a rotatable part for rotation by a user and an axially moveable part connected to the safety pin for moving the safety pin between the actuation locked and safety released positions, wherein the thread and the cooperating groove are disposed between the rotatable part and the axially moveable part. This item relates particularly to the second embodiment.

21. The injector of item 20, wherein the groove is defined in an outer surface of the axially movable part and the thread is defined on an inner surface of the rotatable part. This item relates particularly to the second embodiment.

22. The injector of any preceding item, wherein the injector comprises a safety pin mover that is operable to move the safety pin between the actuation locked position and the safety released position.

23. The injector of item 22, wherein the safety pin mover comprises a rotatable part to affect axial movement of the safety pin between the actuation locked and safety released positions.

24. The injector of item 23, wherein the rotatable part of the safety pin mover is manually graspable to affect at least part of the rotational movement thereof.

25. The injector of item 23 or 24, the safety pin mover comprising a helical or diagonal, relative to the longitudinal axis, thread or groove or other guide structure for transmitting rotational movement of the rotatable part of the safety pin mover to axial movement of the safety pin. This item relates particularly to the first and second embodiments.

26. The injector of any one of the preceding items, structurally defining at least one of first and second stop positions corresponding respectively to the actuation locked position of the safety pin and the safety released position of the safety pin.

27. The injector of item 26 as dependent on any one of items 22 to 25, wherein the first and second stop positions correspond to stop positions for movement of a part of the safety pin mover, preferably wherein the part of the safety pin mover is a movable part that is user operable to move the safety pin between the actuation locked position and the safety released position or the rotatable part of item 23.

28. The injector of item 26 or 27, comprising a groove, a thread, a slot or other guide structure and complementary structure for running along the groove, thread, slot or other guide structure between the first and second stop positions.

29. The injector of item 28 as dependent on any one of items 22 to 25 or 27, the guide and complementary structure comprise a groove and a complementary projection defined between the housing, which is comprised in the safety pin mover, and the safety pin mover or a groove and a complementary thread defined between an axially translatable part of the safety pin mover and a rotatable part of the safety pin mover. This item relates particularly to the first and second embodiments.

30. The injector of item 27, comprising a detent arrangement for releasably holding the part of the safety pin mover in at least one of the first and second stop positions.

31. The injector of item 30, wherein the detent arrangement comprises a cooperating snap fit mechanism, a ledge, a rib or other protruding structure and complementary interacting protrusion, or a recess and complementary protrusion.

32. The injector of item 30 or 31, wherein a first part of the detent arrangement is disposed on a rotatable part of the safety pin mover and a complementary interacting part is associated with a non-rotating part of the safety pin mover, such as the housing of the injector or an axially translatable part of the safety pin mover.

33. The injector of item 23 and item 11 or 12 and item 14 or 15, wherein the safety pin mover comprises the guide and the complementary structure, which are arranged in the sleeve of the safety cap and the housing of the injector and the safety cap itself is rotatable to provide the rotatable part of the safety pin mover. This item particularly relates to the first embodiment.

34. The injector of item 22 or any one of items 23 to 33, wherein the safety pin mover comprises an axially movable, preferably translatable, part and the safety pin mover comprises a rotatable part that cooperate so that rotation of the rotatable part causes axial translation of the axially translatable part, to thereby axially translate the safety pin from the actuation locked position to the safety released position. This item particularly relates to the second embodiment.

35. The injector of item 34 and any one of items 8 to 13, wherein the safety cap comprises the safety pin mover.

36. The injector of item 34 or 35, wherein the rotatable part is mounted for rotation without axial movement.

37. The injector of item 34, 35 or 36, wherein the safety pin is fixed to the axially translatable part. This item particularly relates to the second embodiment.

38. The injector of item 34, 35, 36 or 37 as dependent on any one of items 8 to 13, wherein the safety cap comprises at least one axially extending guide that cooperates with the axially translatable part to guide axial movement of the axially translatable part. This item particularly relates to the second embodiment.

39. The injector of any one of items 34 to 38, wherein the axially translatable part and the rotatable part threadably cooperate to transform rotation of the rotatable part to axial translation of the axially translatable part. This item particularly relates to the second embodiment.

40. The injector of item 8, wherein the safety cap itself or the safety cap and the housing comprise a nut and thread arrangement or other cooperating structure operable to transform rotational input from a user to axial movement of the safety pin between the actuation locked and safety released positions. This item particularly relates to the first and second embodiments.

41. The injector of any one of the preceding items, wherein the injector comprises an indicator for visually indicating when the safety pin is in the safety released position.

42. The injector of any one of the preceding items, wherein the injector comprises an indicator for visually indicating when the safety pin is in the actuation locked position.

43. The injector of any one of the preceding items, comprising an indicator for visually indicating when the safety pin is in the actuation locked position and when the safety pin is in the safety released position in a visually differentiable manner.

44. The injector of item 43 and item 22 or 23, wherein the indicator comprises a moving portion fixedly associated with a movable part, e.g. the rotatable part, of the safety pin mover for aligning with or exposing a first stationary portion of the indicator when the safety pin mover is in a position corresponding to the safety released position of the safety pin.

45. The injector of item 44, wherein the indicator comprises a second stationary portion visually differentiable from the first stationary portion, wherein the moving portion is aligned with or exposes the second stationary portion when the movable part of the safety pin mover is in a first position corresponding to the actuation locked position.

46. The injector of item 44 or 45, wherein the moving portion comprises a window or a tab or wherein the moving portion comprises a cover that covers the first stationary portion when the safety pin mover is in the actuation locked position.

47. The injector of item 22 or any item dependent thereon, wherein the safety pin mover comprises a ribbed gripping surface.

48. The injector of any preceding item dependent thereon, comprising a spring for biasing the safety pin from the actuation locked position to the safety released position.

49. The injector of item 48, comprising a detent arrangement for holding the safety pin in the actuation locked position against the bias of the spring.

50. The injector of item 49, wherein the spring is operable so as to move automatically the safety pin to the safety released position once the detent arrangement has been released.

51. The injector of item 49 or 50, wherein the spring is held in a contracted position by the detent arrangement and is expandable to move the safety pin from the actuation locked position to the safety released position.

52. The injector of item 8 or any preceding item dependent thereon, wherein the safety cap remains axially stationary and is operable to move the safety pin between the actuation locked and safety released positions within the safety cap. This item particularly relates to the second and third embodiments.

53. The injector of any preceding item, wherein the safety pin is moveable from the actuation locked position to the safety released position by translation along the longitudinal axis. This item particularly relates to the first and second embodiments.

54. The injector of any preceding item, comprising an actuator for actuating the injection operation and the safety pin is configured to lock the actuator in the actuation locked position and is configured to release the locking to allow operation of the actuator in the safety released position.

55. The injector of item 5, wherein the actuator comprises an engaged detent mechanism that is disengageable to actuate the injection operation, wherein the detent mechanism is locked to prevent disengagement by the safety pin being in an actuation locked position, and wherein the safety pin is movable to the safety released position in which the detent mechanism is still engaged, yet the detent mechanism is unlocked and is thus able to be disengaged to actuate the injection operation.

56. The injector of item 54, wherein the actuator comprises at least one resilient arm that is deflectable to release from a holding surface to actuate the injection operation with the injector, wherein the safety pin is configured to block deflection of the at least one resilient arm in the actuation locked position and to free deflection of the at least one resilient arm in the safety released position.

57. The injector of item 56, wherein the at least one resilient arm comprises plural resilient arms that are deflectable toward one another to release from a holding surface to actuate the injection operation of the injector, wherein the safety pin is configured to block deflection of the resilient arms toward one another in the actuation locked position and to allow such deflection in the safety released position.

58. The injector of item 57, wherein the resilient arms are comprised in a collet of the injector.

59. The injector of item 57 or 58, wherein the resilient arms define a passage therebetween, wherein the safety pin extends into the passage in the actuation locked position.

60. The injector of item 55, wherein the detent mechanism comprises a collet and collet retention surface from which the collet is disengagable to actuate the injection operation, wherein the safety pin is disposed so as to lock the collet in an engaged position with the collet retention surface when the safety pin is in the actuation locked position and to allow disengagement when the safety pin is in the safety released position.

61. The injector of item 60, wherein the collet comprises detent teeth that engage the retention surface, thereby forming a latch, and the teeth are disengagable from the retention surface to actuate the injection operation, wherein the safety pin is operable to keep the detent teeth apart when in the actuation locked position to lock the detent teeth in engagement with the retention surface.

62. The injector of any one of items 54 to 61, wherein the actuator comprises an outer housing of the injector that is axially moveable relative to the front end of the injector to actuate the injection operation.

63. The injector of item 62 as dependent on item 55, wherein the relative movement of the outer housing is operable to disengage the detent mechanism.

64. The injector of item 62 as dependent on item 56, wherein the relative movement of the outer housing is operable to deflect the at least one resilient arm to disengage the holding arm from the holding surface.

65. The injector of any one of the preceding items, wherein the injection operation of the injector is actuatable by pressing the front end of the injector against an injection site when the safety pin is in the safety released position 66. The injector of any one of the preceding items, wherein the injector is an autoinjector.

67. The injector of item 66, comprising a cartridge containing a medicament, the needle, a plunger and a driver for providing a drive force to move the needle from a retracted position relative to the front end of the injector to an extended position, wherein a front end of the needle extends beyond the front end of the injector, and to drive the plunger to eject medicament from the cartridge through the needle when the needle is in the extended position.

68. The injector of item 67, wherein the cartridge has a closed front end prior to actuation of the injector and an open rear for receiving the plunger.

69. The injector of item 67 or 68, wherein the cartridge and the needle are moveable in conjunction by the driving force.

70. The injector of item 67, 68 or 69, wherein the cartridge is moveable by the driving force from a position spaced from a rear end of the needle to a position in which the medicament in the cartridge is in fluid communication with the rear end of the needle, and thereafter the needle and the cartridge are moveable by the driving force in conjunction to move the needle from the retracted position to the extended position.

71. The injector of any one of items 67 to 70, comprising a needle cover that is moveable between a retracted position to a needle covering position when the needle is in the extended position.

72. The injector of item 71, wherein the autoinjector is configured to automatically move the needle cover from the retracted position to the needle covering position upon actuation of the autoinjector.

73. The injector of item 71 or 72, comprising a first locking mechanism for locking the needle cover in the retracted position and a second locking mechanism for locking the needle cover in the extended position, wherein the injector is configured, upon actuation, to unlock the first locking mechanism to allow the needle cover to move to the extended position from the retracted position and to operate the second locking mechanism to lock the needle cover in the extended position for preventing exposure of the needle after the injection operation and after the autoinjector has been moved away from the injection site.

74. The injector of item 71, 72 or 73, comprising a needle cover spring for driving movement of the needle cover from the retracted position to the extended position.
75. The injector of item 74 as dependent on item 73, wherein the needle cover spring is able to drive movement of the needle cover when the first locking mechanism is unlocked.
76. The injector of any preceding item, wherein the front end of the injector comprises a plugged or sealed opening through which the needle of the injector extends during the injection operation, wherein the needle is configured to pierce the plug or seal during the injection operation.
77. The injector of any one of items 1 to 66, wherein the injector comprises a driver held in a relatively high potential energy state and is configured so that the potential energy is realised after actuation of the injection operation to drive the injection operation automatically.
78. The injector of item 77, wherein the driver comprises a spring configured to be held in a compressed state until actuation and is expandable upon actuation to drive the injection operation.
79. The injector of any one of items 1 to 66, 77 or 78, wherein the injector comprises a medicament source and the needle, and the injection operation comprises penetration of the needle at the injection site and injection of medicament from the medicament source.
80. The injector of item 79, wherein the medicament source is a cartridge.
81. The injector of item 79 or 80, wherein the medicament source contains adrenalin for injection.
82. The injector of any preceding item, wherein the injector is for treatment of anaphylaxis and contains medicament prescribed therefor.
83. The injector of any one of the preceding items, wherein the injector comprises an outer housing for grasping by a user.
84. The injector of item 83 and item 71, wherein the needle cover is disposed at least partly within the outer housing in the retracted and in the extended positions.
85. The injector of item 83 and item 71, comprising a cartridge housing and the needle cover is disposed at least partly between the outer housing and the cartridge housing in both the retracted and the extended positions.
86. The injector of item 85 and item 73, wherein the first and/or the second locking mechanisms are disposed between the cartridge housing and the outer housing.
87. The injector of item 8 or any one of item 9 to 86 as dependent on item 8, wherein the safety cap is engaged with the housing to prevent rearward movement thereof when the safety pin is in the safety released position.
88. The injector of item 87, comprising interfacing holding surfaces between the housing and the safety cap for preventing movement of the safety cap in the rearward direction when the safety pin is in the safety released position.
89. A safety cap comprising a sleeve for receiving a rear end portion of a housing of an injector for mounting the safety cap to the injector, a safety pin for extending through an opening in a rear end face of the housing of the injector to lock an actuator of the injector, and a safety pin mover, wherein the safety pin mover comprises at least one of a thread and structure for cooperating with the thread to transform rotational movement of a rotatable part of the safety pin mover to rearward axial movement of the safety pin for rearwardly moving the safety pin from an actuation locked position in locking relation with the actuator to a safety released position in which the actuator is unlocked by the safety pin. This item and the following items 90 to 107 relate particularly to the second embodiment.
90. The safety cap of item 89, wherein the rotatable part of the safety pin mover is rotatable to affect axial translation of the safety pin.
91. The safety cap of item 89 or 90, wherein the rotatable part of the safety pin mover is rotatably mounted relative to the sleeve.
92. The safety cap of item 89, 90 or 91, wherein the safety pin is mounted for axial movement relative to the sleeve.
93. The safety cap of any one of items 89 to 92, wherein the sleeve is adapted for resilient snap fit mounting to the housing of the injector.
94. The safety cap of any one of items 89 to 93, wherein the safety cap comprises an axially translatable part to which the safety pin is fixed and which cooperates with the rotatable part of the safety pin mover through the thread and thread cooperating structure such that rotation of the safety pin mover causes translation of the safety pin.
95. The safety cap of any one of items 89 to 94, wherein the safety cap comprises a visual indication part in fixed relation with the rotatable part of the safety pin mover, wherein the visual indication part comprises a relatively coloured area, a flag, a tab, a window, an icon or other visual indicia for indicating when the safety pin is in the safety released position.
96. The safety cap of any one of items 89 to 95, wherein the safety cap comprises complementary visual indicator parts including a moving part that is in fixed relation with the rotatable part of the safety pin mover and first and second stationary parts that are visually distinct, wherein the moving part aligns with the first stationary part when the safety pin is in the actuation locked position and wherein the moving part aligns with the second stationary part when the safety pin is in the safety released position.
97. The safety cap of any one of items 89 to 96, wherein the safety pin and the sleeve are coaxially arranged.
98. The safety cap of any one of items 89 to 96, wherein the safety cap comprises a closed rear cover portion at least in an area axially aligned with a longitudinal axis of the safety pin.
99. The safety cap of any one of items 89 to 98, wherein the rotatable part of the safety pin mover comprises ribs for enhancing a user's grip thereof.
100. The safety cap of any one of items 89 to 99, wherein the rotatable part of the safety pin mover is externally accessible for being gripped and rotated by a user.
101. The safety cap of any one of items 89 to 100, wherein the rotatable part of the safety pin mover is rotatable between first and second stop positions corresponding respectively to the safety pin being in the actuation locked position and the safety pin being in the safety released position.
102. The safety cap of item 101, wherein the safety cap comprises at least one of first and second detent arrangements for holding the first and second stop positions and requiring a force bump to release the at least of first and second detent arrangements.
103. The safety cap of any one of items 89 to 102, wherein the safety cap comprises a spring for biasing the safety pin to the safety released position.
104. The safety cap of any one of items 89 to 103, wherein the pin and the sleeve define a loop shaped space therebetween into which the rear end portion of the housing of the injector is able to be inserted to mount the safety cap to the injector.
105. The safety cap of any one of items 89 to 104, wherein the thread comprises a rib arranged as a thread or a groove arranged as a thread.

106. The safety cap of item 105, wherein the thread extends helically or diagonally.

107. The safety cap of item 105 or 106, wherein the cooperating structure comprises a groove for receiving the rib formed as a thread to allow the rib to ride in the groove or a projection for riding in the groove formed as a thread.

108. The injector of item 1 and other items dependent on item 1, wherein the safety pin is part of a safety cap that is mounted on an outside of the injector housing.

109. The injector of item 108, wherein the safety cap is rotatable to affect rotation of the safety pin to move the safety pin between the actuation locked and safety released positions.

110. The injector of item 108 or 109, wherein the safety pin comprises one or more blocking surfaces and one or more recesses that are circumferentially distributed, wherein the blocking surfaces engage a part of an actuator of the injector to block actuation of the actuator and the recesses release the part of the actuator of the injector to allow actuation of the actuator, wherein rotation of the safety pin is able to align the blocking surfaces with the part of the actuator and is able to align the recesses with the part of the actuator to respectively provide actuation ready and actuation locked states for the injector.

111. The injector of item 110, wherein the part of the actuator is at least one resilient arm thereof.

The invention claimed is:

1. An injector for performing an injection operation comprising a housing, a needle extendable from a front end of the housing, a rear end of the housing and a longitudinal axis extending between the front end and the rear end, and a safety cap comprising a safety pin, wherein the safety pin extends through an opening in a rear end face of and wherein the safety pin is in an actuation locked position coupled to the housing and is moveable to a safety released position coupled to the housing, wherein the injector is locked against actuation when the safety, pin is in the actuation locked position and the injector is ready for actuation of the injection operation when the safety pin is in the safety released position; and wherein the safety cap itself or the housing and the safety cap comprise cooperating structure operable to transform rotational input from a user to axial movement of the safety pin between the actuation locked and safety released positions.

2. The injector of claim 1, wherein the opening is covered by the safety cap comprising the safety pin when the safety pin is in the safety released position.

3. The injector of claim 1, wherein the safety pin is elongate and extends along the longitudinal axis of the injector.

4. The injector of claim 1, wherein the safety cap covers a rear end face of the housing, and wherein the safety cap has a closed rear surface in an area longitudinally aligned with a rear end of the safety pin.

5. The injector of claim 4, wherein the safety cap comprises a sleeve extending over a rear end portion of the housing of the injector.

6. The injector of claim 1, comprising a guide and structure cooperating with the guide to guide movement of the safety pin between the actuation locked position and the safety released position, wherein the guide extends from a first position corresponding to the actuation locked position and a second position corresponding to the safety released position.

7. The injector of claim 1, comprising an actuator for actuating the injection operation and the safety pin is configured to lock the actuator in the actuation locked position and is configured to release the lock to allow operation of the actuator in the safety released position.

8. The injector of claim 7, wherein the actuator comprises at least one resilient arm that is deflectable to release from a holding surface to actuate the injection operation with the injector, wherein the safety pin is configured to block deflection of the at least one resilient arm in the actuation locked position and to free deflection of the at least one resilient arm in the safety released position.

9. The injector of claim 1, comprising a safety pin mover that is manually operable to move the safety pin between the actuation locked position and the safety released position.

10. The injector of claim 9, wherein the safety pin mover comprises a rotatable part operable by a user, to move the safety pin between the actuation locked and safety released positions, wherein the rotatable part of the safety pin mover is externally positioned on the injector to allow manual grasping to affect at least part of the rotational movement thereof.

11. The injector of claim 10, wherein the safety cap itself is rotatable to provide the rotatable part of the safety pin mover, and wherein the safety cap is configured for moving conjointly axially and rotationally for axially moving the safety pin between the actuation locked and safety released positions.

12. The injector of claim 10, wherein the safety pin mover comprises an axially translatable part and the safety pin mover comprises the rotatable part that cooperate so that rotation of the rotatable part causes axial translation of the axially translatable part, to thereby axially translate the safety pin from the actuation locked position to the safety released position, wherein the rotatable part is mounted for rotation without axial movement.

13. The injector of claim 1, wherein the safety cap comprises a spring for biasing the safety pin from the actuation locked position to the safety released position.

14. The injector of claim 1, structurally defining at least one of first and second stop positions corresponding respectively to the actuation locked position of the safety pin and the safety released position of the safety pin.

15. The injector of claim 1, comprising an indicator for visually indicating when the safety pin is in the actuation locked position and when the safety pin is in the safety released position in a visually differentiable manner.

16. An injector for performing an injection operation comprising a housing, a needle extendable from a front end of the housing, a rear end of the housing and a longitudinal axis extending between the front end and the rear end, a safety pin in an actuation locked position coupled to the housing and moveable to a safety released position coupled to the housing, wherein the safety pin extends through an opening in a rear end face of the housing, and the needle of the injector is extendable through a front end face of the housing, and wherein the injector is locked against actuation when the safety pin is in the actuation locked position and the injector is ready for actuation of the injection operation when the safety pin is in the safety released position, the injector further comprising a spring for biasing the safety pin from the actuation locked position to the safety released position.

17. The injector of item 16, comprising a detent arrangement for holding the safety pin in the actuation locked position against the bias of the spring.

18. The injector of item 17, wherein the spring is operable so as to move automatically the safety pin to the safety released position once the detent arrangement has been released.

* * * * *